US009220612B2

(12) United States Patent
Behzadi

(10) Patent No.: US 9,220,612 B2
(45) Date of Patent: Dec. 29, 2015

(54) PROSTHESIS POSITIONING SYSTEMS AND METHODS

(71) Applicant: Kambiz Behzadi, Pleasanton, CA (US)

(72) Inventor: Kambiz Behzadi, Pleasanton, CA (US)

( * ) Notice: Subject to any disclaimer, the term of this patent is extended or adjusted under 35 U.S.C. 154(b) by 0 days.

(21) Appl. No.: 14/585,056

(22) Filed: Dec. 29, 2014

(65) Prior Publication Data

US 2015/0182351 A1     Jul. 2, 2015

Related U.S. Application Data

(63) Continuation-in-part of application No. 14/584,656, filed on Dec. 29, 2014.

(60) Provisional application No. 61/980,188, filed on Apr. 16, 2014, provisional application No. 61/921,528, filed on Dec. 29, 2013.

(51) Int. Cl.
*A61F 2/46* (2006.01)
*A61B 17/17* (2006.01)
*A61B 17/34* (2006.01)
*A61B 17/88* (2006.01)

(52) U.S. Cl.
CPC ............ *A61F 2/4609* (2013.01); *A61B 17/1742* (2013.01); *A61B 17/3468* (2013.01); *A61B 17/88* (2013.01); *A61F 2002/4632* (2013.01)

(58) Field of Classification Search
CPC ............... A61B 17/88; A61B 17/1742; A61B 17/3468; A61F 2/4609
See application file for complete search history.

(56) References Cited

U.S. PATENT DOCUMENTS

| | | |
|---|---|---|
| 5,019,083 A | 5/1991 | Klapper et al. |
| 5,061,270 A | 10/1991 | Aboczky |
| 5,112,338 A | 5/1992 | Anspach, III |
| 5,169,399 A | 12/1992 | Ryland et al. |
| 5,236,433 A | 8/1993 | Salyer |
| 5,456,686 A | 10/1995 | Klapper et al. |
| 5,540,697 A | 7/1996 | Rehmann et al. |
| 5,571,111 A | 11/1996 | Aboczky |
| 5,683,395 A | 11/1997 | Mikhail |
| 6,228,092 B1 | 5/2001 | Mikhail |
| 6,723,102 B2 | 4/2004 | Johnson et al. |
| 6,884,264 B2 | 4/2005 | Spiegelberg et al. |
| 6,917,827 B2 | 7/2005 | Kienzle, III |
| 7,326,217 B2 | 2/2008 | Bubb |

(Continued)

FOREIGN PATENT DOCUMENTS

| | | |
|---|---|---|
| WO | 9740785 | 11/1997 |
| WO | 0108569 A1 | 2/2001 |

(Continued)

OTHER PUBLICATIONS

The WoodPecker, Total Hip Broaching System, General Information, 1992, [retrieved on Feb. 13, 2015] , Retrieved from the Internet: <www.imt-medicalusa.com/products/woodpecker-hip-broaching-system.aspx>.

(Continued)

*Primary Examiner* — Andrew Yang
(74) *Attorney, Agent, or Firm* — Patent Law Offices of Michael E. Woods; Michael E. Woods

(57) ABSTRACT

A system and method for improving positioning of a prosthesis, particularly prostheses having a preferred orientation with respect to a frame of reference of a patient.

17 Claims, 28 Drawing Sheets

(56) References Cited

U.S. PATENT DOCUMENTS

| | | |
|---|---|---|
| 7,559,931 B2 | 7/2009 | Stone |
| 7,604,637 B2 | 10/2009 | Johnson et al. |
| 7,645,281 B2 | 1/2010 | Marik |
| 7,727,282 B2 | 6/2010 | Slone et al. |
| 8,057,479 B2 | 11/2011 | Stone |
| 8,128,631 B2 | 3/2012 | Johnson et al. |
| 8,167,823 B2 | 5/2012 | Nycz et al. |
| 8,206,405 B2 | 6/2012 | Beverland et al. |
| 8,216,286 B2 | 7/2012 | Aeschlimann et al. |
| 8,496,657 B2 | 7/2013 | Bonutti et al. |
| 8,556,909 B2 | 10/2013 | Giersch et al. |
| 8,801,724 B2 | 8/2014 | Zumsteg et al. |
| 2002/0193797 A1 | 12/2002 | Johnson et al. |
| 2008/0109008 A1 | 5/2008 | Schwager et al. |
| 2011/0251600 A1 | 10/2011 | Giersch et al. |
| 2012/0136361 A1 | 5/2012 | Aux Epaules et al. |
| 2012/0209277 A1 | 8/2012 | Leparmentier et al. |
| 2013/0282014 A1 | 10/2013 | Haimerl et al. |
| 2014/0135791 A1* | 5/2014 | Nikou et al. .................. 606/130 |

FOREIGN PATENT DOCUMENTS

| | | |
|---|---|---|
| WO | 2008003962 A1 | 1/2008 |
| WO | 2015100461 A1 | 7/2015 |

OTHER PUBLICATIONS

The WoodPecker, Total Hip Broaching System, Specification, 1992, [retrieved on Feb. 13, 2015], Retrieved from the Internet: <www.imt-medicalusa.com/products/woodpecker-specifications.aspx>.

The WoodPecker, Total Hip Broaching System, Operation Manual, 1992, [retrieved on Feb. 13, 2015], Retrieved from the Internet: <www.plusmed.si/uploads/datoteke/Pnevmatsko%20kladivo%20-%2Onavodilo%20za%20uporabo.pdf>.

The WoodPecker, Total Hip Broaching System, YourTube Reference—Total Hip Replacement with The Woodpecker Pneumatic Broaching System (2002), Uploaded Nov. 4, 2009, [retrieved on Feb. 13, 2015], Retrieved from the Internet: <www.youtube.com/watch?v=KisN6__M-xS0>.

* cited by examiner

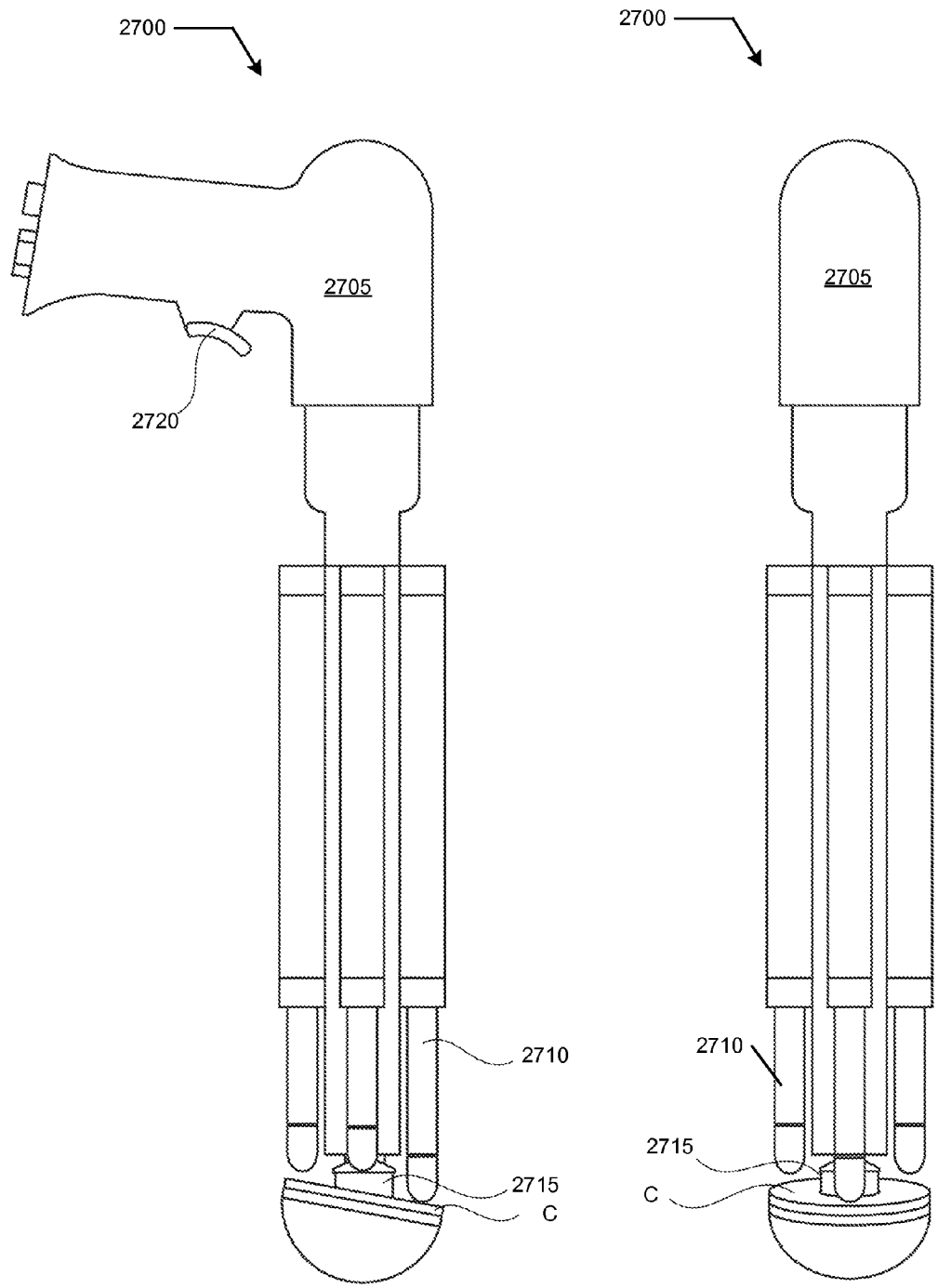
*FIG. 27*  *FIG. 28*

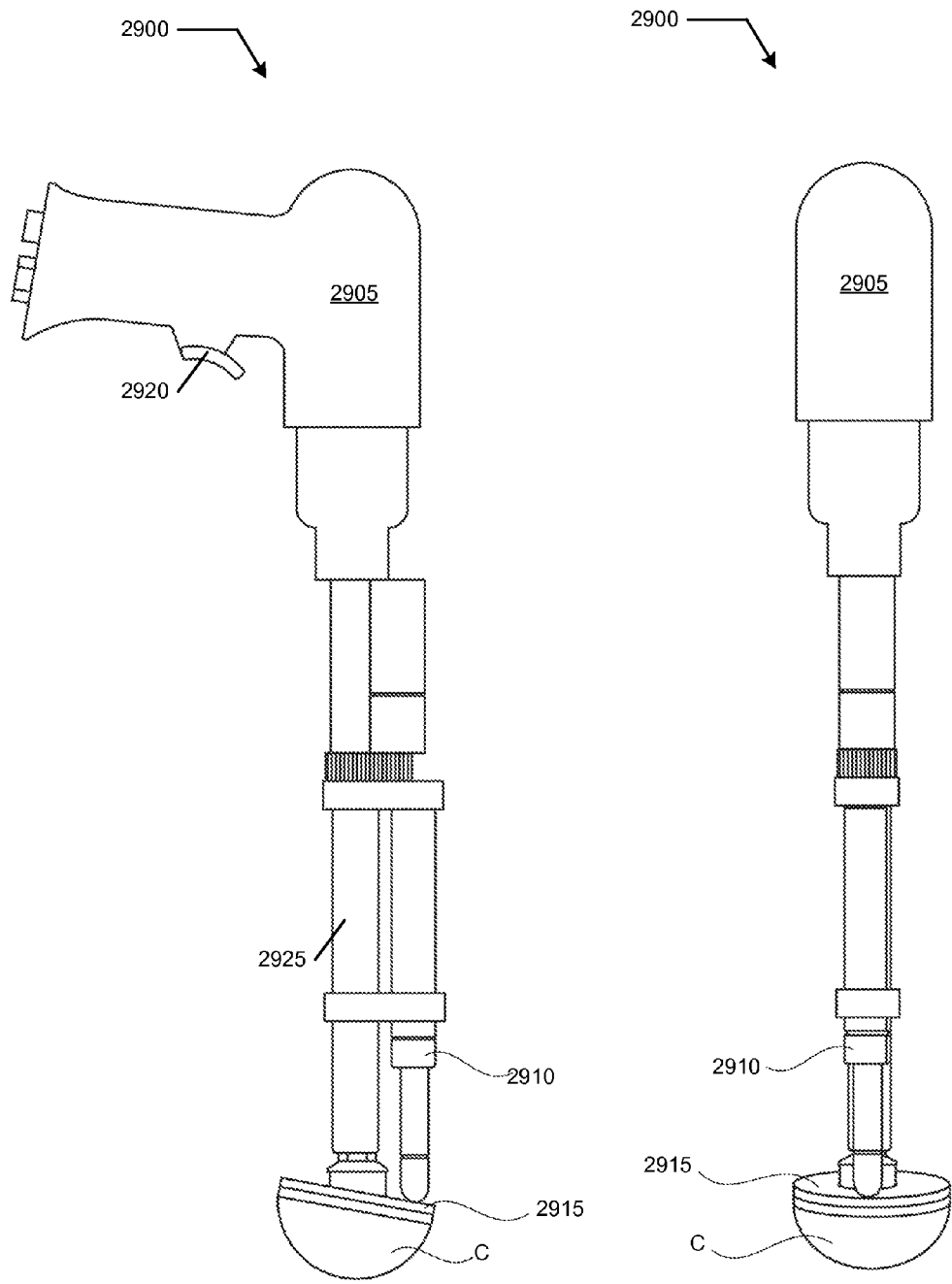
FIG. 29  FIG. 30

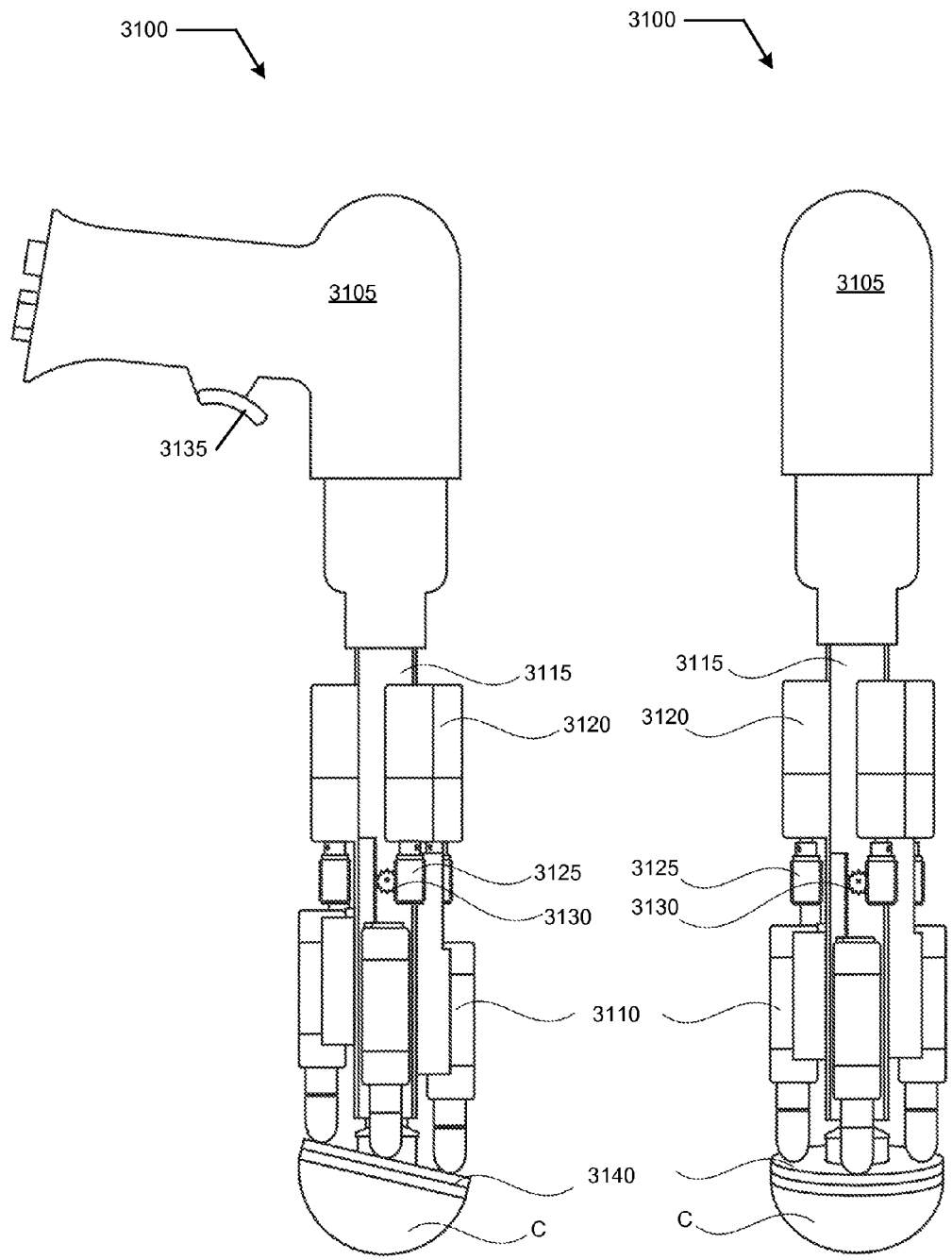
*FIG. 31*  *FIG. 32*

PROSTHESIS POSITIONING SYSTEMS AND METHODS

CROSS REFERENCE TO RELATED APPLICATIONS

This application is a continuation-in-part of U.S. patent application Ser. No. 14/584,656 and claims benefit of both U.S. Patent Application No. 61/921,528 and U.S. Patent Application No. 61/980,188, the contents in their entireties are hereby expressly incorporated by reference thereto for all purposes.

FIELD OF THE INVENTION

The present invention relates generally to orthopedic surgical systems and procedures employing a prosthetic implant for, and more specifically, but not exclusively, to joint replacement therapies such as total hip replacement including controlled installation and positioning of the prosthesis such as during replacement of a pelvic acetabulum with a prosthetic implant.

BACKGROUND OF THE INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Total hip replacement refers to a surgical procedure where a hip joint is replaced using a prosthetic implant. There are several different techniques that may be used, but all include a step of inserting an acetabular component into the acetabulum and positioning it correctly in three dimensions (along an X, Y, and Z axis).

In total hip replacement (THR) procedures there are advantages to patient outcome when the procedure is performed by a surgeon specializing in these procedures. Patients of surgeons who do not perform as many procedures can have increased risks of complications, particularly of complications arising from incorrect placement and positioning of the acetabular component.

The incorrect placement and positioning may arise even when the surgeon understood and intended the acetabular component to be inserted and positioned correctly. This is true because in some techniques, the tools for actually installing the acetabular component are crude and provide an imprecise, unpredictable coarse positioning outcome.

It is known in some techniques to employ automated and/or computer-assisted navigation tools, for example, x-ray fluoroscopy or computer guidance systems. There are computer assisted surgery techniques that can help the surgeon in determining the correct orientation and placement of the acetabular component. However, current technology provides that at some point the surgeon is required to employ a hammer/mallet to physically strike a pin or alignment rod. The amount of force applied and the location of the application of the force are variables that have not been controlled by these navigation tools. Thus even when the acetabular component is properly positioned and oriented, when actually impacting the acetabular component into place the actual location and orientation can differ from the intended optimum location and orientation. In some cases the tools used can be used to determine that there is, in fact, some difference in the location and/or orientation. However, once again the surgeon must employ an impacting tool (e.g., the hammer/mallet) to strike the pin or alignment rod to attempt an adjustment. However the resulting location and orientation of the acetabular component after the adjustment may not be, in fact, the desired location and/or orientation. The more familiar that the surgeon is with the use and application of these adjustment tools can reduce the risk to a patient from a less preferred location or orientation. In some circumstances, quite large impacting forces are applied to the prosthesis by the mallet striking the rod; these forces make fine tuning difficult at best and there is risk of fracturing and/or shattering the acetabulum during these impacting steps.

What is needed is a system and method for improving positioning of a prosthesis, particularly prostheses having a preferred orientation with respect to a frame of reference of a patient.

BRIEF SUMMARY OF THE INVENTION

Disclosed is a system and method for improving positioning of a prosthesis, particularly prostheses having a preferred orientation with respect to a frame of reference of a patient.

The following summary of the invention is provided to facilitate an understanding of some of technical features related to total hip replacement, and is not intended to be a full description of the present invention. A full appreciation of the various aspects of the invention can be gained by taking the entire specification, claims, drawings, and abstract as a whole. The present invention is applicable to other surgical procedures, including replacement of other joints replaced by a prosthetic implant in addition to replacement of an acetabulum (hip socket) with an acetabular component (e.g., a cup). Use of pneumatic and electric motor implementations have both achieved a proof of concept development.

The disclosed concepts involve creation of a system/method/tool/gun that vibrates an attached prosthesis, e.g., an acetabular cup. The gun would be held in a surgeon's hands and deployed. It would use a vibratory energy to insert (not impact) and position the cup into desired alignment (using current intra-operation measurement systems, navigation, fluoroscopy, and the like).

In one embodiment, a first gun-like device is used for accurate impaction of the acetabular component at the desired location and orientation.

In another embodiment, a second gun-like device is used for fine-tuning of the orientation of the acetabular component, such as one installed by the first gun-like device, by traditional mallet and tamp, or by other methodology. However the second gun-like device may be used independently of the first gun-like device for adjusting an acetabular component installed using an alternate technique. Similarly the second gun-like device may be used independently of the first gun-like device, particularly when the initial installation is sufficiently close to the desired location and orientation. These embodiments are not necessarily limited to fine-tuning as certain embodiments permit complete re-orientation. Some implementations allow for removal of an installed prosthesis.

Another embodiment includes a third gun-like device that combines the functions of the first gun-like device and the second gun-like device. This embodiment enables the surgeon to accurately locate, insert, orient, and otherwise position the acetabular component with the single tool.

Another embodiment includes a fourth device that installs the acetabular component without use of the mallet and the rod, or use of alternatives to strike the acetabular component for impacting it into the acetabulum. This embodiment imparts a vibratory motion to an installation rod coupled to the acetabular component that enables low-force, impactless installation and/or positioning.

A positioning device for an acetabular cup disposed in a bone, the acetabular cup including an outer shell having a sidewall defining an inner cavity and an opening with the sidewall having a periphery around the opening and with the acetabular cup having a desired abduction angle relative to the bone and a desired anteversion angle relative to the bone, including a controller including a trigger and a selector; a support having a proximal end and a distal end opposite of the proximal end, the support further having a longitudinal axis extending from the proximal end to the distal end with the proximal end coupled to the controller, the support further having an adapter coupled to the distal end with the adapter configured to secure the acetabular cup; and a number N, the number N, an integer greater than or equal to 2, of longitudinal actuators coupled to the controller and disposed around the support generally parallel to the longitudinal axis, each the actuator including an associated impact head arranged to strike a portion of the periphery, each impact head providing an impact strike to a different portion of the periphery when the associated actuator is selected and triggered; wherein each the impact strike adjusts one of the angles relative to the bone.

An installation device for an acetabular cup disposed in a pelvic bone, the acetabular cup including an outer shell having a sidewall defining an inner cavity and an opening with the sidewall having a periphery around the opening and with the acetabular cup having a desired installation depth relative to the bone, a desired abduction angle relative to the bone, and a desired anteversion angle relative to the bone, including a controller including a trigger; a support having a proximal end and a distal end opposite of said proximal end, said support further having a longitudinal axis extending from said proximal end to said distal end with said proximal end coupled to said controller, said support further having an adapter coupled to said distal end with said adapter configured to secure the acetabular cup; and an oscillator coupled to said controller and to said support, said oscillator configured to control an oscillation frequency and an oscillation magnitude of said support with said oscillation frequency and said oscillation magnitude configured to install the acetabular cup at the installation depth with the desired abduction angle and the desired anteversion angle without use of an impact force applied to the acetabular cup.

An installation system for a prosthesis configured to be implanted into a portion of bone at a desired implantation depth, the prosthesis including an attachment system, including an oscillation engine including a controller coupled to a vibratory machine generating an original series of pulses having a generation pattern, said generation pattern defining a first duty cycle of said original series of pulses; and a pulse transfer assembly having a proximal end coupled to said oscillation engine and a distal end, spaced from said proximal end, coupled to the prosthesis with said pulse transfer assembly including a connector system at said proximal end, said connector system complementary to the attachment system and configured to secure and rigidly hold the prosthesis producing a secured prosthesis with said pulse transfer assembly communicating an installation series of pulses, responsive to said original series of pulses, to said secured prosthesis producing an applied series of pulses responsive to said installation series of pulses; wherein said applied series of pulses are configured to impart a vibratory motion to said secured prosthesis enabling an installation of said secured prosthesis into the portion of bone to within 95% of the desired implantation depth without a manual impact.

A method for installing an acetabular cup into a prepared socket in a pelvic bone, the acetabular cup including an outer shell having a sidewall defining an inner cavity and an opening with the sidewall having a periphery around the opening and with the acetabular cup having a desired installation depth relative to the bone, a desired abduction angle relative to the bone, and a desired anteversion angle relative to the bone, including (a) generating an original series of pulses from an oscillation engine; (b) communicating said original series of pulses to the acetabular cup producing a communicated series of pulses at said acetabular cup; (c) vibrating, responsive to said communicated series of pulses, the acetabular cup to produce a vibrating acetabular cup having a predetermined vibration pattern; and (d) inserting the vibrating acetabular cup into the prepared socket within a first predefined threshold of the installation depth with the desired abduction angle and the desired anteversion angle without use of an impact force applied to the acetabular cup.

This method may further include (e) orienting the vibrating acetabular cup within the prepared socket within a second predetermined threshold of the desired abduction angle and within third predetermined threshold of the desired anteversion angle.

A method for inserting a prosthesis into a prepared location in a bone of a patient at a desired insertion depth wherein non-vibratory insertion forces for inserting the prosthesis to the desired insertion depth are in a first range, the method including (a) vibrating the prosthesis using a tool to produce a vibrating prosthesis having a predetermined vibration pattern; and (b) inserting the vibrating prosthesis into the prepared location to within a first predetermined threshold of the desired insertion depth using vibratory insertion forces in a second range, said second range including a set of values less than a lowest value of the first range.

Any of the embodiments described herein may be used alone or together with one another in any combination. Inventions encompassed within this specification may also include embodiments that are only partially mentioned or alluded to or are not mentioned or alluded to at all in this brief summary or in the abstract. Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

Other features, benefits, and advantages of the present invention will be apparent upon a review of the present disclosure, including the specification, drawings, and claims.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIG. 12 illustrates the reference frame and the orthogonal axes;

FIG. 13 illustrates the orthogonal axes with an associated frontal plane and a transverse plane; and FIG. 14 illustrates a different perspective view of the orthogonal axes with the associated frontal plane and a transverse plane.

FIG. 19 illustrates a representative positioning gun;

FIG. 20 illustrates a left-hand detail of the positioning gun of FIG. 19;

FIG. 21 illustrates a right-hand detail of the positioning gun of 19 and generally when combined with FIG. 20 produces the illustration of FIG. 19;

FIG. 22 illustrates an initial condition of the pre-positioned installed prosthesis with respect to an impact ring installed on a positioning system;

FIG. 23 illustrates an intermediate condition of the pre-positioned installed prosthesis with respect to the impact ring installed on a positioning system; and FIG. 24 illustrates a final condition having a positioned installed prosthesis with respect to the impact ring installed on a positioning system.

FIG. 27-FIG. 34 illustrate alternate embodiments for a positioning systems employing an impact ring model;

FIG. 27-FIG. 28 illustrate a first alternate embodiment for a positioning system;

FIG. 27 illustrates a side view of the first alternate embodiment; and

FIG. 28 illustrates a top view of the first alternate embodiment; and

FIG. 29-FIG. 30 illustrate a second alternate embodiment for a positioning system;

FIG. 29 illustrates a side view of the second alternate embodiment; and

FIG. 30 illustrates a top view of the second alternate embodiment; and

FIG. 31-FIG. 32 illustrate a third alternate embodiment for a positioning system;

FIG. 31 illustrates a side view of the third alternate embodiment; and

FIG. 32 illustrates a top view of the third alternate embodiment; and

FIG. 33 illustrates a side view of a fourth alternate embodiment for a positioning system; and FIG. 34 illustrates a side view of a fifth alternate embodiment for a positioning system.

DETAILED DESCRIPTION OF THE INVENTION

Figure 1:
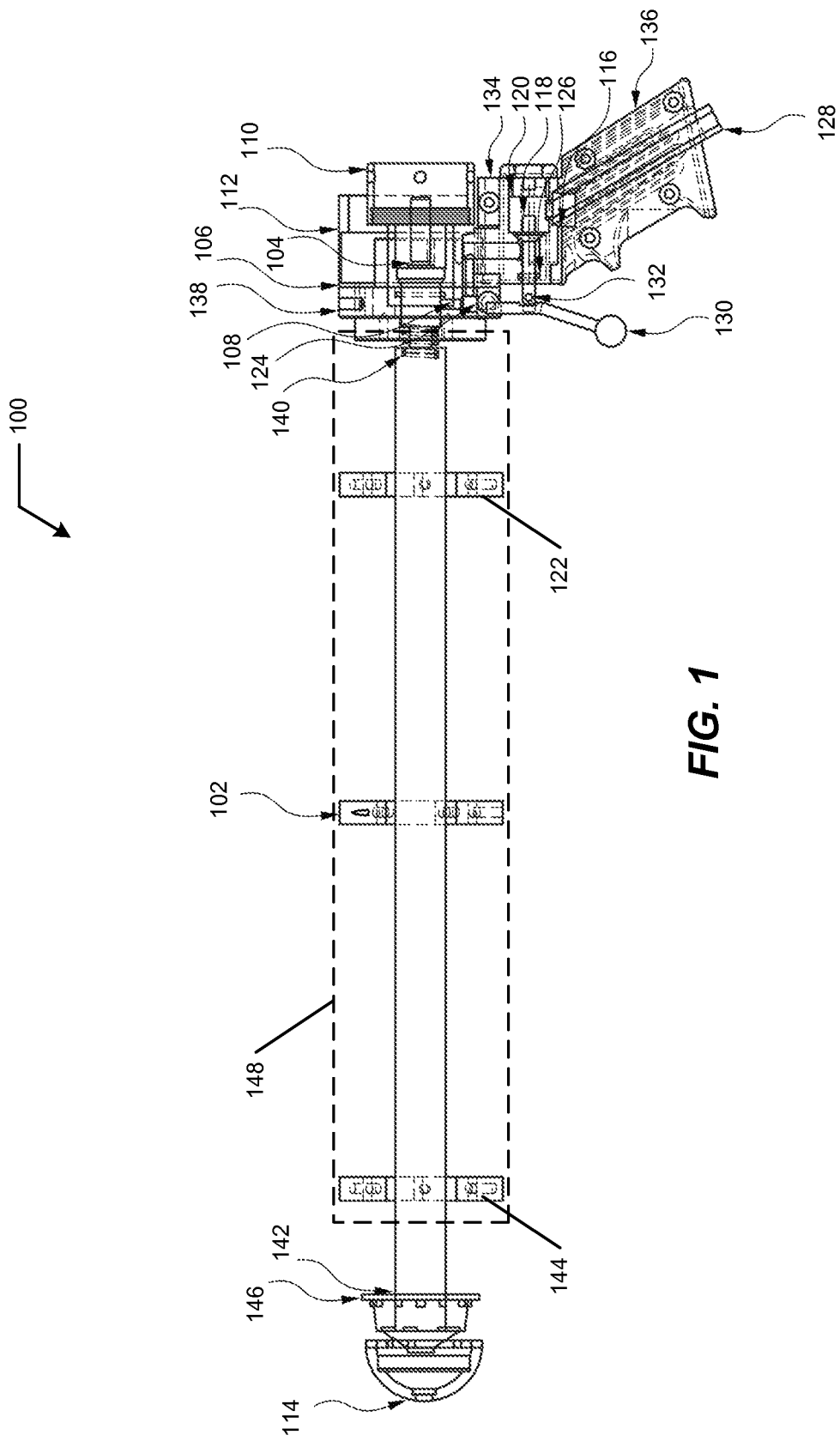
FIG. 1 illustrates a representative installation gun.

Embodiments of the present invention provide a system and method for improving positioning of a prosthesis, particularly prostheses having a preferred orientation with respect to a frame of reference of a patient. The following description is presented to enable one of ordinary skill in the art to make and use the invention and is provided in the context of a patent application and its requirements.

Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

DEFINITIONS

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The following definitions apply to some of the aspects described with respect to some embodiments of the invention. These definitions may likewise be expanded upon herein.

As used herein, the term "or" includes "and/or" and the term "and/or" includes any and all combinations of one or more of the associated listed items. Expressions such as "at least one of," when preceding a list of elements, modify the entire list of elements and do not modify the individual elements of the list.

As used herein, the singular terms "a," "an," and "the" include plural referents unless the context clearly dictates otherwise. Thus, for example, reference to an object can include multiple objects unless the context clearly dictates otherwise.

Also, as used in the description herein and throughout the claims that follow, the meaning of "in" includes "in" and "on" unless the context clearly dictates otherwise. It will be understood that when an element is referred to as being "on" another element, it can be directly on the other element or intervening elements may be present therebetween. In contrast, when an element is referred to as being "directly on" another element, there are no intervening elements present.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common properties.

As used herein, the term "adjacent" refers to being near or adjoining. Adjacent objects can be spaced apart from one another or can be in actual or direct contact with one another. In some instances, adjacent objects can be coupled to one another or can be formed integrally with one another.

As used herein, the terms "connect," "connected," and "connecting" refer to a direct attachment or link. Connected objects have no or no substantial intermediary object or set of objects, as the context indicates.

As used herein, the terms "couple," "coupled," and "coupling" refer to an operational connection or linking. Coupled objects can be directly connected to one another or can be indirectly connected to one another, such as via an intermediary set of objects.

As used herein, the terms "substantially" and "substantial" refer to a considerable degree or extent. When used in conjunction with an event or circumstance, the terms can refer to instances in which the event or circumstance occurs precisely as well as instances in which the event or circumstance occurs to a close approximation, such as accounting for typical tolerance levels or variability of the embodiments described herein.

As used herein, the terms "optional" and "optionally" mean that the subsequently described event or circumstance may or may not occur and that the description includes instances where the event or circumstance occurs and instances in which it does not.

As used herein, the term "bone" means rigid connective tissue that constitute part of a vertebral skeleton, including mineralized osseous tissue, particularly in the context of a living patient undergoing a prosthesis implant into a portion of cortical bone. A living patient, and a surgeon for the patient, both have significant interests in reducing attendant risks of conventional implanting techniques including fracturing/shattering the bone and improper installation and positioning of the prosthesis within the framework of the patient's skeletal system and operation.

As used herein, the term "size" refers to a characteristic dimension of an object. Thus, for example, a size of an object that is spherical can refer to a diameter of the object. In the case of an object that is non-spherical, a size of the non-spherical object can refer to a diameter of a corresponding spherical object, where the corresponding spherical object exhibits or has a particular set of derivable or measurable properties that are substantially the same as those of the non-spherical object. Thus, for example, a size of a non-spherical object can refer to a diameter of a corresponding spherical object that exhibits light scattering or other properties that are substantially the same as those of the non-spherical object. Alternatively, or in conjunction, a size of a non-spherical object can refer to an average of various orthogonal dimensions of the object. Thus, for example, a size of an object that is a spheroidal can refer to an average of a major axis and a minor axis of the object. When referring to a set of objects as having a particular size, it is contemplated that the objects can have a distribution of sizes around the particular size. Thus, as used herein, a size of a set of objects can refer to a typical size of a distribution of sizes, such as an average size, a median size, or a peak size.

As used herein, mallet or hammer refers to an orthopedic device made of stainless steel or other dense material having a weight generally a carpenter's hammer and a stonemason's lump hammer.

As used herein, an impact force for impacting an acetabular component (e.g., an acetabular cup prosthesis) includes forces from striking an impact rod multiple times with the orthopedic device that are generally similar to the forces that may be used to drive a three inch nail into a piece of lumber using the carpenter's hammer by striking the nail approximately a half-dozen times to completely seat the nail. Without limiting the preceding definition, a representative value in some instances includes a force of approximately 10 lbs/square inch.

The following description relates to improvements in a wide-range of prostheses installations into live bones of patients of surgeons. The following discussion focuses primarily on total hip replacement (THR) in which an acetabular cup prosthesis is installed into the pelvis of the patient. This cup is complementary to a ball and stem (i.e., a femoral prosthesis) installed into an end of a femur engaging the acetabulum undergoing repair.

As noted in the background, the surgeon prepares the surface of the hipbone which includes attachment of the acetabular prosthesis to the pelvis. Conventionally, this attachment includes a manual implantation in which a mallet is used to strike a tamp that contacts some part of the acetabular prosthesis. Repeatedly striking the tamp drives the acetabular prosthesis into the acetabulum. Irrespective of whether current tools of computer navigation, fluoroscopy, robotics (and other intra-operative measuring tools) have been used, it is extremely unlikely that the acetabular prosthesis will be in the correct orientation once it has been seated to the proper depth by the series of hammer strikes. After manual implantation in this way, the surgeon then may apply a series of adjusting strikes around a perimeter of the acetabular prosthesis to attempt to adjust to the desired orientation. Currently such post-impaction result is accepted as many surgeons believe that post-impaction adjustment creates an unpredictable and unreliable change which does not therefore warrant any attempts for post-impaction adjustment.

In most cases, any and all surgeons including an inexperienced surgeon may not be able to achieve the desired orientation of the acetabular prosthesis in the pelvis by conventional solutions due to unpredictability of the orientation changes responsive to these adjusting strikes. As noted above, it is most common for any surgeon to avoid post-impaction adjustment as most surgeons understand that they do not have a reliable system or method for improving any particular orientation and could easily introduce more/greater error. The computer navigation systems, fluoroscopy, and other measuring tools are able to provide the surgeon with information about the current orientation of the prosthesis (in real time) during an operation and after the prosthesis has been installed and its deviation from the desired orientation, but the navigation systems (and others) do not protect against torsional forces created by the implanting/positioning strikes. The prosthesis will find its own position in the acetabulum based on the axial and torsional forces created by the blows of the mallet. Even those navigation systems used with robotic systems (e.g., MAKO) that attempt to secure an implant in the desired orientation prior to impaction are not guaranteed to result in the installation of the implant at the desired orientation because the actual implanting forces are applied by a surgeon swinging a mallet to manually strike the tamp.

A Behzadi Medical Device (BMD) is herein described and enabled that eliminates this crude method (i.e., mallet, tamp, and surgeon-applied mechanical implanting force) of the prosthesis (e.g., the acetabular cup). A surgeon using the BMD is able to insert the prosthesis exactly where desired with proper force, finesse, and accuracy. Depending upon implementation details, the installation includes insertion of the prosthesis into patient bone, within a desired threshold of metrics for insertion depth and location) and may also include, when appropriate and/or desired, positioning at a desired orientation with the desired threshold further including metrics for insertion orientation). The use of the BMD reduces risks of fracturing and/or shattering the bone receiving the prosthesis and allows for rapid, efficient, and accurate (atraumatic) installation of the prosthesis. The BMD provides a viable interface for computer navigation assistance (also useable with all intraoperative measuring tools including fluoroscopy) during the installation as a lighter more responsive touch may be used.

The BMD encompasses many different embodiments for installation and/or positioning of a prosthesis and may be adapted for a wide range of prostheses in addition to installation and/or positioning of an acetabular prosthesis during THR.

Figure 2:
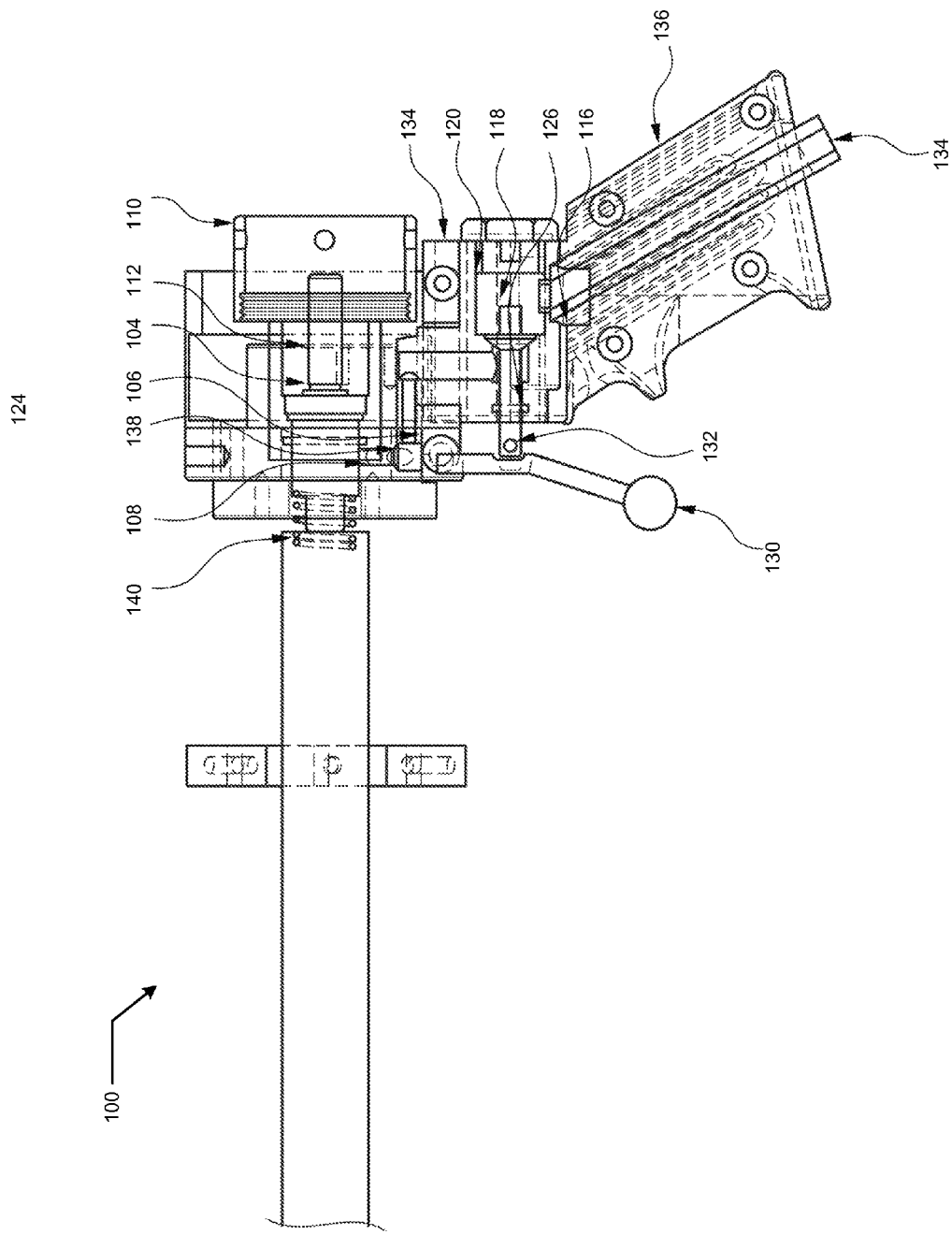
FIG. 2 illustrates a right-hand detail of the installation gun of FIG. 1.
Figure 3:
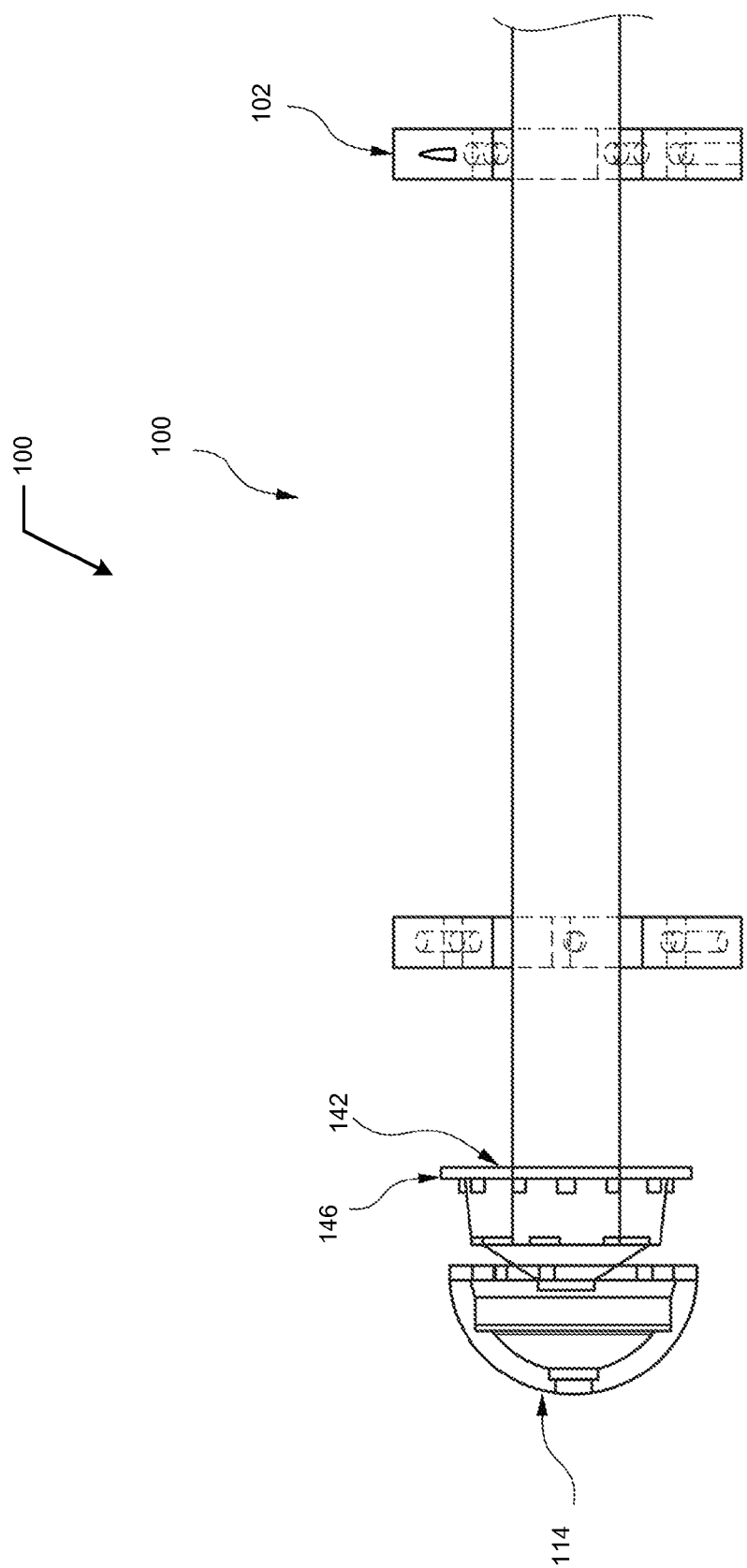
FIG. 3 illustrates a left-hand detail of the installation gun of FIG. 1 and generally when combined with FIG. 2 produces the illustration of FIG. 1.

FIG. 1 illustrates a representative installation gun 100; FIG. 2 illustrates a right-hand detail of the installation gun 100; and FIG. 3 illustrates a left-hand detail of installation gun of 100 and generally when combined with FIG. 2 produces the illustration of FIG. 1. Installation gun 100 is represented as operable using pneumatics, though other implementations may use other mechanisms for creating a desired vibratory motion of prosthesis to be installed.

Installation gun 100 is used to control precisely one or both of (i) insertion, and (ii) abduction and anteversion angles of a prosthetic component. Installation gun 100 preferably allows both installation of an acetabular cup into an acetabulum at a desired depth and orientation of the cup for both abduction and anteversion to desired values. The following reference numbers in Table I refer to elements identified in FIG. 1-FIG. 3:

TABLE I

Device 100 Elements

| | |
|---|---|
| 102 | Middle guide housing |
| 104 | Klip |
| 106 | Kuciste |
| 108 | CILINDAR |
| 110 | Cjev |
| 112 | Poklopac |
| 114 | 54 mm acetabular cup |
| 116 | Body |
| 118 | Valve |
| 120 | Bottom cap |
| 122 | Upper guide housing |
| 124 | Handle cam |
| 126 | DIN 3771 6 × 1,8-N-NBR 70 |
| 128 | Main Air Inlet - Input Tube |
| 130 | Trigger |
| 132 | Trigger pin |
| 134 | DIN 3771 6 × 1,8-N-NBR 70 |
| 136 | MirrorAR15 - Hand Grip 1 |
| 138 | Crossover Tube |
| 140 | 9657K103 compression spring |
| 142 | Elongate tube |
| 144 | Lower guide housing |
| 146 | Primary adapter |
| 148 | Housing |

Installation gun 100 includes a controller with a handle supporting an elongate tube 142 that terminates in adapter 146 that engages cup 114. Operation of trigger 130 initiates a motion of elongate tube 142. This motion is referred to herein as an installation force and/or installation motion that is much less than the impact force used in a conventional replacement process. An exterior housing 148 allows the operator to hold and position prosthesis 114 while elongate tube 142 moves within. Some embodiments may include a handle or other grip in addition to or in lieu of housing 148 that allows the operator to hold and operate installation gun 100 without interfering with the mechanism that provides a direct transfer of installation motion to prosthesis 114. The illustrated embodiment includes prosthesis 114 held securely by adapter 146 allowing a tilting and/or rotation of gun 100 about any axis to be reflected in the position/orientation of the secured prosthesis.

The installation motion includes constant, cyclic, periodic, and/or random motion (amplitude and/or frequency) that allows the operator to install cup 114 into the desired position (depth and orientation) without application of an impact force. There may be continuous movement or oscillations in one or more of six degrees of freedom including translation(s) and/or rotation(s) of adapter 146 about the X, Y, Z axes (e.g., oscillating translation(s) and/or oscillating/continuous rotation(s) which could be different for different axes such as translating back and forth in the direction of the longitudinal axis of the central support while rotating continuously around the longitudinal axis). This installation motion may include continuous or intermittent very high frequency movements and oscillations of small amplitude that allow the operator to easily install the prosthetic component in the desired location, and preferably also to allow the operator to also set the desired angles for abduction and anteversion.

In some implementations, the controller includes a stored program processing system that includes a processing unit that executes instructions retrieved from memory. Those instructions could control the selection of the motion parameters autonomously to achieve desired values for depth, abduction and anteversion entered into by the surgeon or by a computer aided medical computing system such as the computer navigation system. Alternatively those instructions could be used to supplement manual operation to aid or suggest selection of the motion parameters.

For more automated systems, consistent and unvarying motion parameters are not required and it may be that a varying dynamic adjustment of the motion parameters better conform to an adjustment profile of the cup installed into the acetabulum and status of the installation. An adjustment profile is a characterization of the relative ease by which depth, abduction and anteversion angles may be adjusted in positive and negative directions. In some situations these values may not be the same and the installation gun could be enhanced to adjust for these differences. For example, a unit of force applied to pure positive anteversion may adjust anteversion in the positive direction by a first unit of distance while under the same conditions that unit of force applied to pure negative anteversion may adjust anteversion in the negative direction by a second unit of distance different from the first unit. And these differences may vary as a function of the magnitude of the actual angle(s). For example, as the anteversion increases it may be that the same unit of force results in a different responsive change in the actual distance adjusted. The adjustment profile when used helps the operator when selecting the actuators and the impact force(s) to be applied. Using a feedback system of the current real-time depth and orientation enables the adjustment profile to dynamically select/modify the motion parameters appropriately during different phases of the installation. One set of motion parameters may be used when primarily setting the depth of the implant and then another set used when the desired depth is achieved so that fine tuning of the abduction and anteversion angles is accomplished more efficiently, all without use of impact forces in setting the depth and/or angle adjustment(s).

This device better enables computer navigation as the installation/adjustment forces are reduced as compared to the impacting method. This makes the required forces more compatible with computer navigation systems used in medical procedures which do not have the capabilities or control systems in place to actually provide impacting forces for seating the prosthetic component. And without that, the computer is at best relegated to a role of providing after-the-fact assessments of the consequences of the surgeon's manual strikes of the orthopedic mallet. (Also provides information before and during the impaction. It is a problem that the very act of impaction introduces variability and error in positioning and alignment of the prosthesis.

Figure 4:
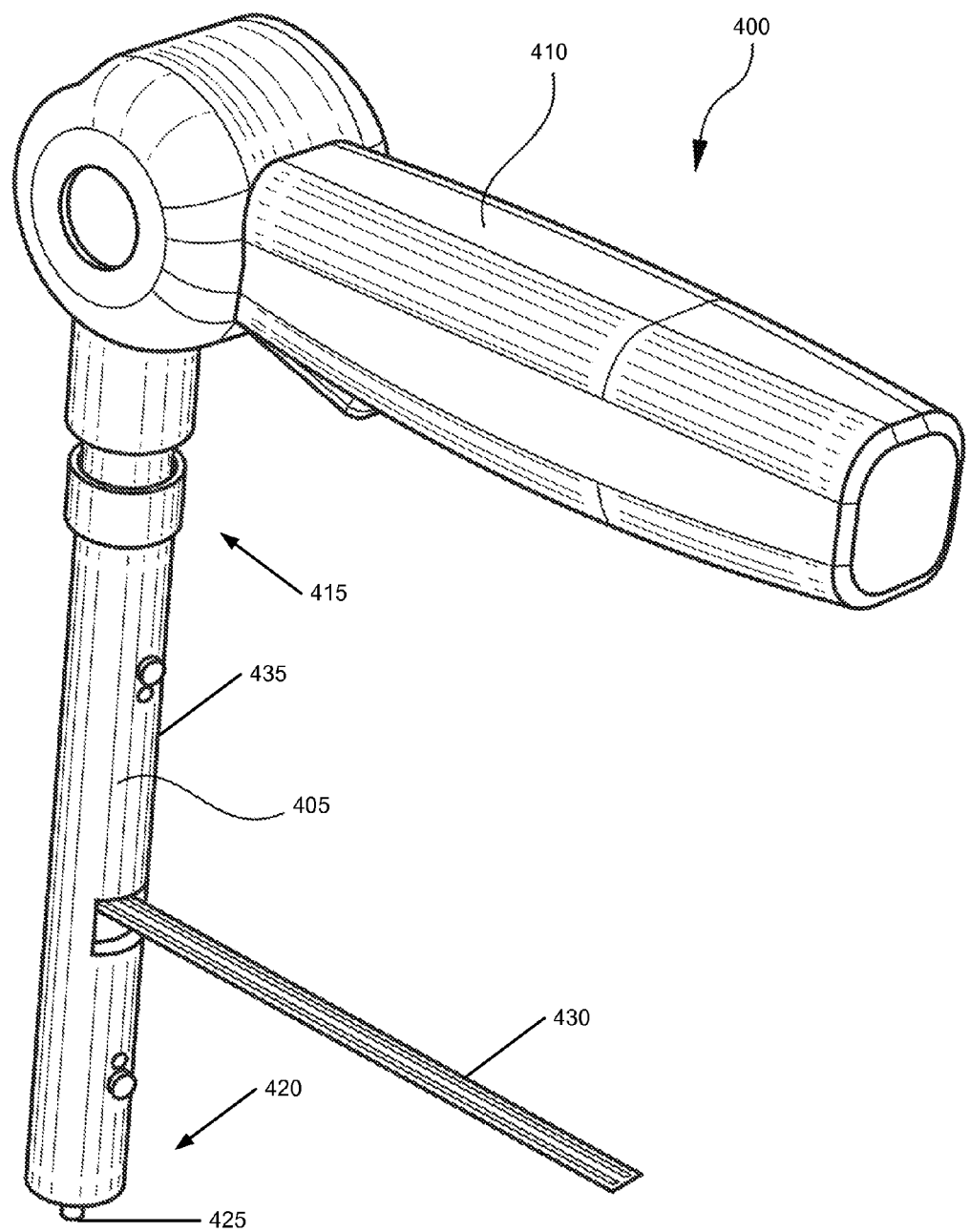
FIG. 4 illustrates a second representative installation system.
Figure 5:
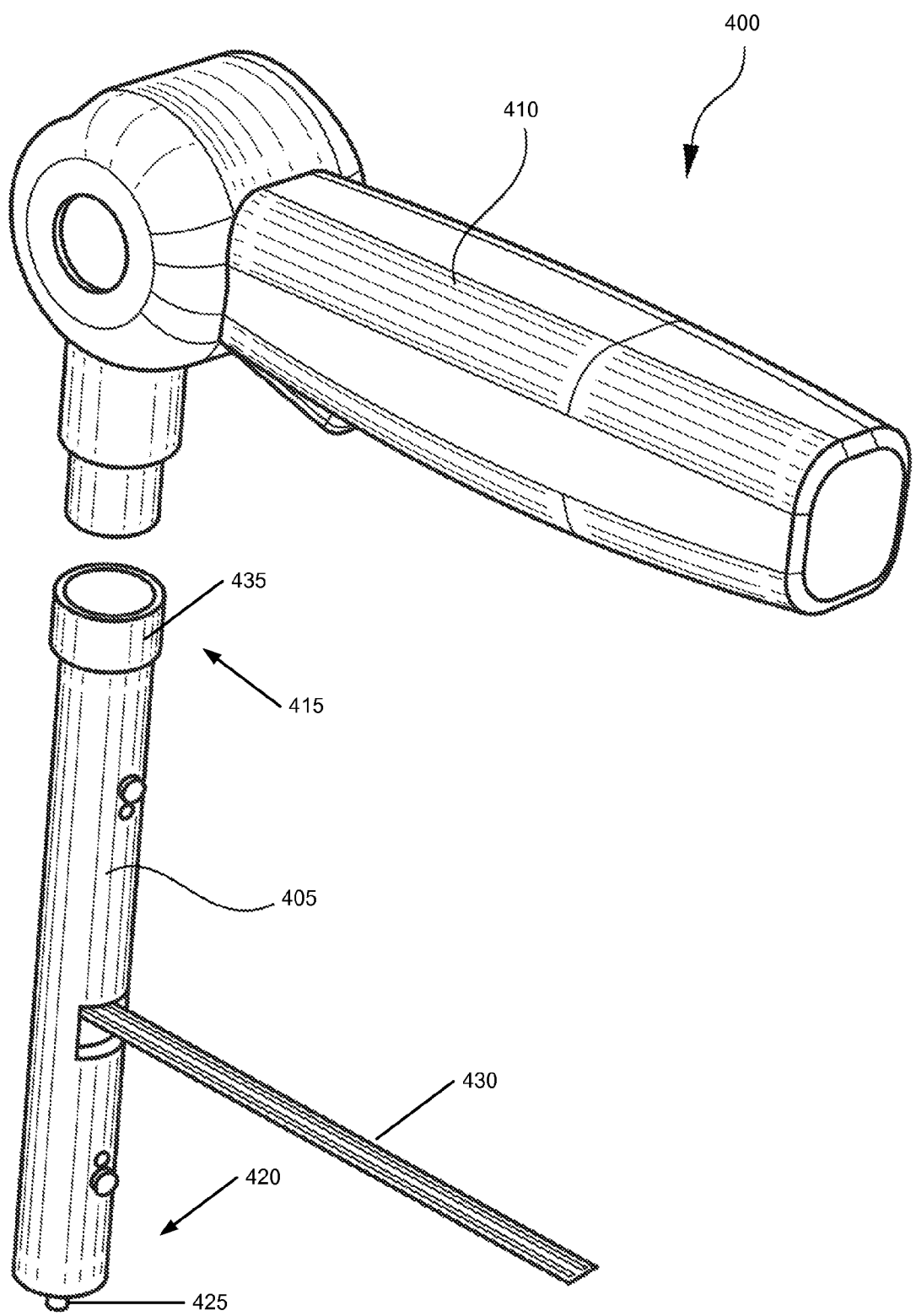
FIG. 5 illustrates a disassembly of the second representative installation system of FIG. 4.
Figure 6:
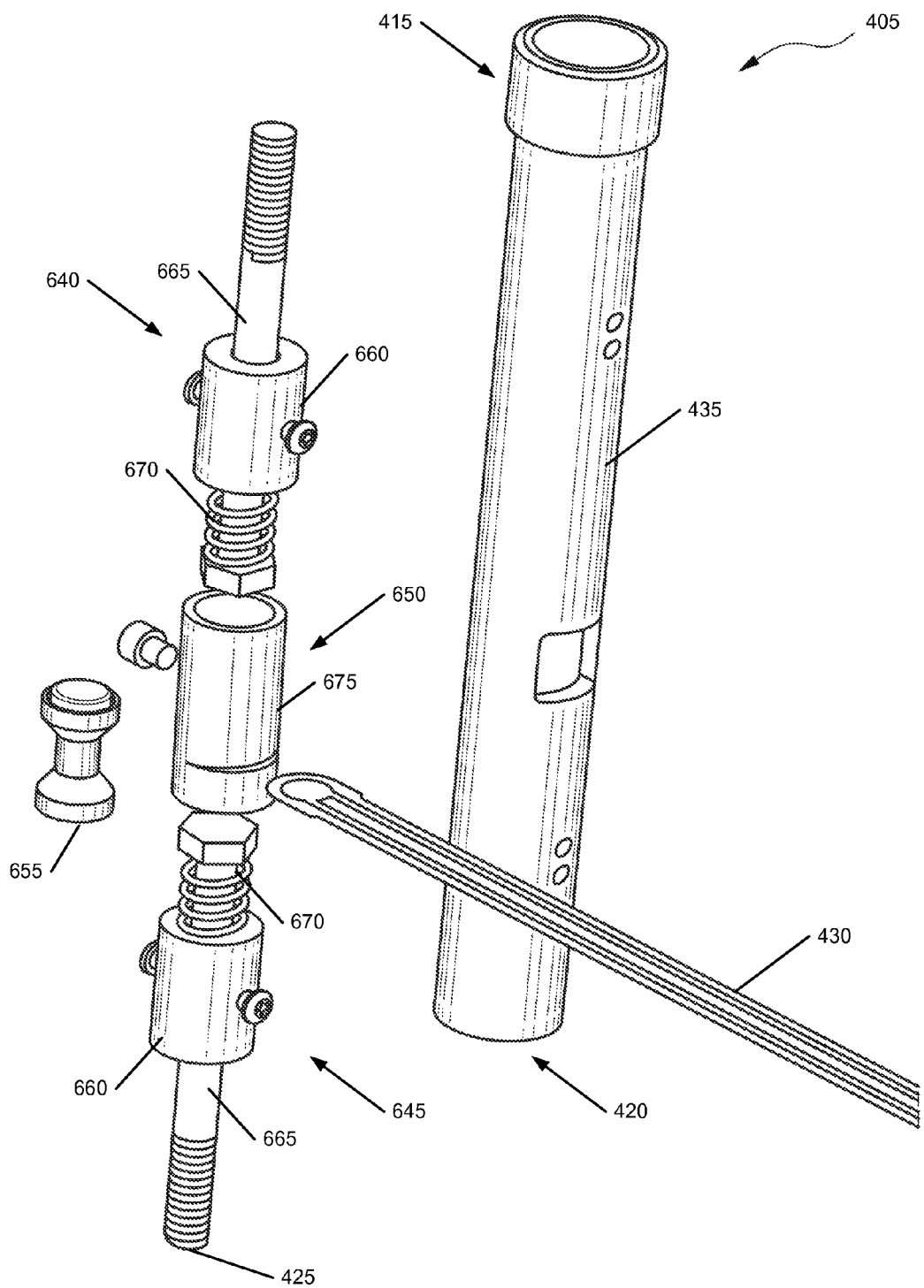
FIG. 6 illustrates a first disassembly view of the pulse transfer assembly of the installation system of FIG. 4.
Figure 7:
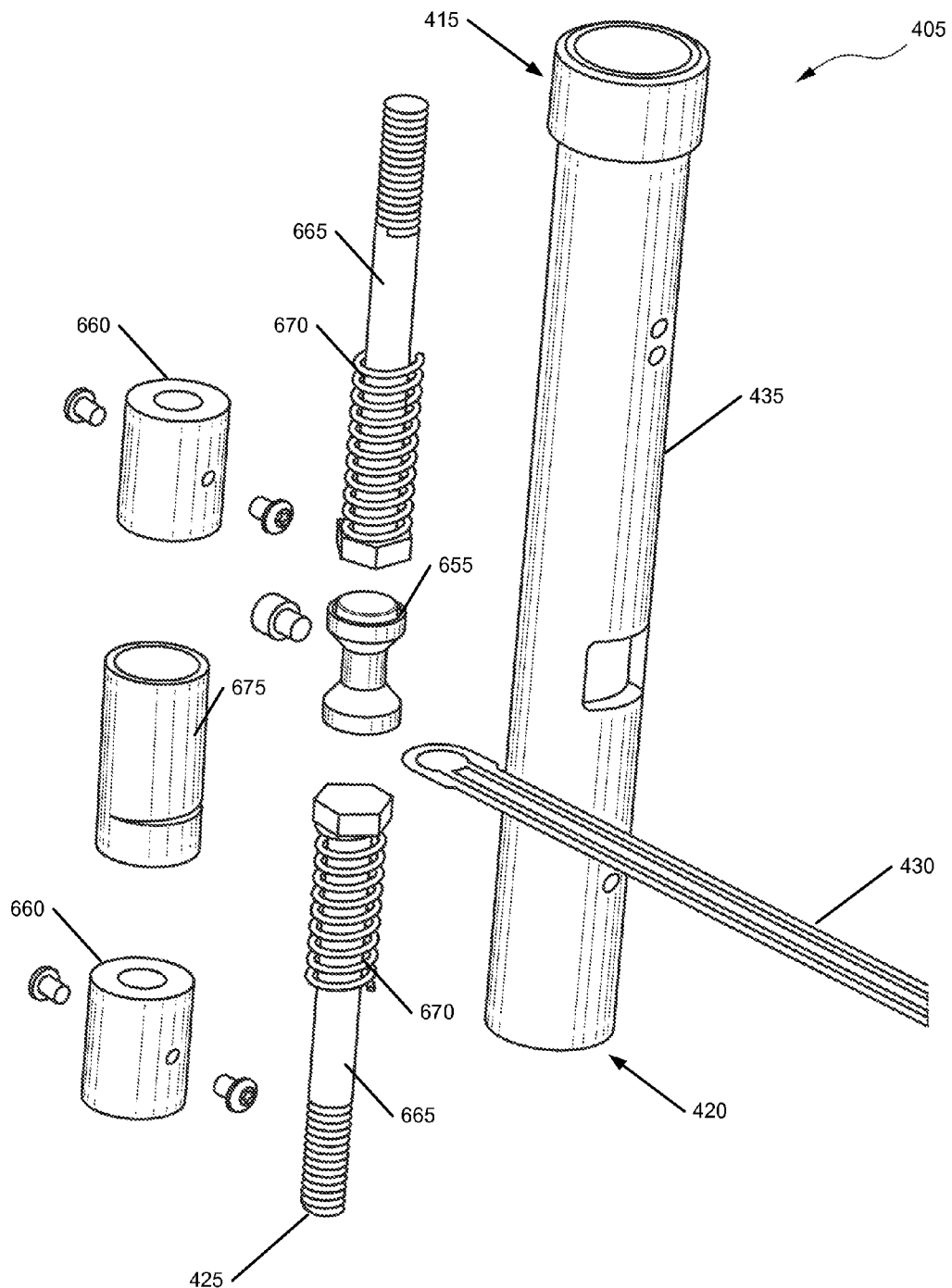
FIG. 7 illustrates a second disassembly view of the pulse transfer assembly of the installation system of FIG. 4.

FIG. 4 illustrates a second representative installation system 400 including a pulse transfer assembly 405 and an oscillation engine 410; FIG. 5 illustrates a disassembly of second representative installation system 400; FIG. 6 illustrates a first disassembly view of pulse transfer assembly 405; and FIG. 7 illustrates a second disassembly view of pulse transfer assembly 405 of installation system 400.

Installation system 400 is designed for installing a prosthesis that, in turn, is configured to be implanted into a portion of bone at a desired implantation depth. The prosthesis includes some type of attachment system (e.g., one or more threaded inserts, mechanical coupler, link, or the like) allowing the prosthesis to be securely and rigidly held by an object such that a translation and/or a rotation of the object about any axis results in a direct corresponding translation and/or rotation of the secured prosthesis.

Oscillation engine 410 includes a controller coupled to a vibratory machine that generates an original series of pulses having a generation pattern. This generation pattern defines a first duty cycle of the original series of pulses including one or more of a first pulse amplitude, a first pulse direction, a first pulse duration, and a first pulse time window. This is not to suggest that the amplitude, direction, duration, or pulse time window for each pulse of the original pulse series are uniform with respect to each other. Pulse direction may include motion having any of six degrees of freedom—translation along one or more of any axis of three orthogonal axes and/or rotation about one or more of these three axes. Oscillation engine 410 includes an electric motor powered by energy from a battery, though other motors and energy sources may be used.

Pulse transfer assembly 405 includes a proximal end 415 coupled to oscillation engine 410 and a distal end 420, spaced from proximal end 420, coupled to the prosthesis using a connector system 425. Pulse transfer assembly 405 receives the original series of pulses from oscillation engine 410 and produces, responsive to the original series of pulses, an installation series of pulses having an installation pattern. Similar to the generation pattern, the installation pattern defines a second duty cycle of the installation series of pulses including a second pulse amplitude, a second pulse direction, a second pulse duration, and a second pulse time window. Again, this is not to suggest that the amplitude, direction, duration, or pulse time window for each pulse of the installation pulse series are uniform with respect to each other. Pulse direction may include motion having any of six degrees of freedom—translation along one or more of any axis of three orthogonal axes and/or rotation about one or more of these three axes.

For some embodiments of pulse transfer assembly 405, the installation series of pulses will be strongly linked to the original series and there will be a close match, if not identical match, between the two series. Some embodiments may include a more complex pulse transfer assembly 405 that produces an installation series that is more different, or very different, from the original series.

Connector system 425 (e.g., one or more threaded studs complementary to the threaded inserts of the prosthesis, or other complementary mechanical coupling system) is disposed at proximal end 420. Connector system 425 is configured to secure and rigidly hold the prosthesis. In this way, the attached prosthesis becomes a secured prosthesis when engaged with connector system 425.

Pulse transfer assembly 405 communicates the installation series of pulses to the secured prosthesis and produces an applied series of pulses that are responsive to the installation series of pulses. Similar to the generation pattern and the installation pattern, the applied pattern defines a third duty cycle of the applied series of pulses including a third pulse amplitude, a third pulse direction, a third pulse duration, and a third pulse time window. Again, this is not to suggest that the amplitude, direction, duration, or pulse time window for each pulse of the applied pulse series are uniform with respect to each other. Pulse direction may include motion having any of six degrees of freedom—translation along one or more of any axis of three orthogonal axes and/or rotation about one or more of these three axes.

For some embodiments of pulse transfer assembly 405, the applied series of pulses will be strongly linked to the original series and/or the installation series and there will be a close, if not identical, match between the series. Some embodiments may include a more complex pulse transfer assembly 405 that produces an applied series that is more different, or very different, from the original series and/or the installation series. In some embodiments, for example one or more components may be integrated together (for example, integrating oscillation engine 410 with pulse transfer assembly 405) so that the first series and the second series, if they exist independently are nearly identical if not identical).

The applied series of pulses are designed to impart a vibratory motion to the secured prosthesis that enable an installation of the secured prosthesis into the portion of bone to within 95% of the desired implantation depth without a manual impact. That is, in operation, the original pulses from oscillation engine 410 propagate through pulse transfer assembly 405 (with implementation-depending varying levels of fidelity) to produce the vibratory motion to the prosthesis secured to connector system 425. In a first implementation, the vibratory motion allows implanting without manual impacts on the prosthesis and in a second mode an orientation of the implanted secured prosthesis may be adjusted by rotations of installation system 400 while the vibratory motion is active, also without manual impact. In some implementations, the pulse generation may produce different vibratory motions optimized for these different modes.

Installation system 400 includes an optional sensor 430 (e.g., a flex sensor or the like) to provide a measurement (e.g., quantitative and/or qualitative) of the installation pulse pattern communicated by pulse transfer assembly 405. This measurement may be used as part of a manual or computerized feedback system to aid in installation of a prosthesis. For example, in some implementations, the desired applied pulse pattern of the applied series of pulses (e.g., the vibrational motion of the prosthesis) may be a function of a particular installation pulse pattern, which can be measured and set through sensor 430. In addition to, or alternatively, other sensors may aid the surgeon or an automated installation system operating installation system 400, such as a bone density sensor or other mechanism to characterize the bone receiving the prosthesis to establish a desired applied pulse pattern for optimal installation.

The disassembled views of FIG. 6 and FIG. 7 detail a particular implementation of pulse transfer assembly 405, it being understood that there are many possible ways of creating and communicating an applied pulse pattern responsive to a series of generation pulses from an oscillation engine. The illustrated structure of FIG. 6 and FIG. 7 generate primarily longitudinal/axial pulses in response to primarily longitudinal/axial generation pulses from oscillation engine 410.

Pulse transfer assembly 405 includes an outer housing 435 containing an upper transfer assembly 640, a lower transfer assembly 645 and a central assembly 650. Central assembly 650 includes a double anvil 655 that couples upper transfer assembly 640 to lower transfer assembly 645. Outer housing 635 and central assembly 650 each include a port allowing sensor 630 to be inserted into central assembly 650 between an end of double anvil 655 and one of the upper/lower transfer assemblies.

Upper transfer assembly 640 and lower transfer assembly 645 each include a support 660 coupled to outer housing 435 by a pair of connectors. A transfer rod 665 is moveably disposed through an axial aperture in each support 660, with each transfer rod 665 including a head at one end configured to strike an end of double anvil 655 and a coupling structure at a second end. A compression spring 670 is disposed on each transfer rod 665 between support 660 and the head. The coupling structure of upper transfer assembly 640 cooperates with oscillation engine 410 to receive the generated pulse series. The coupling structure of lower transfer assembly 645 includes connector system 425 for securing the prosthesis. Some embodiments may include an adapter, not shown, that adapts connector system 425 to a particular prosthesis, different adapters allowing use of pulse transfer assembly 405 with different prosthesis.

Central assembly 650 includes a support 675 coupled to outer housing 435 by a connector and receives double anvil 655 which moves freely within support 675. The heads of the upper transfer assembly and the lower transfer assembly are disposed within support 675 and arranged to strike corresponding ends of double anvil 655 during pulse generation.

In operation, oscillation engine 410 generates pulses that are transferred via pulse transfer assembly 405 to the prosthesis secured by connector system 425. The pulse transfer assembly 405, via upper transfer assembly 640, receives the generated pulses using transfer rod 665. Transfer rod 665 of upper transfer assembly 640 moves within support 660 of upper transfer assembly 640 to communicate pulses to double anvil 655 moving within support 675. Double anvil 655, in turn, communicates pulses to transfer rod 665 of lower transfer assembly 645 to produce vibratory motion of a prosthesis secured to connector system 425. Transfer rods 665 move, in this illustrated embodiment, primarily longitudinally/axially within outer housing 435 (a longitudinal axis defined as extending between proximate end 415 and distal end 420. In this way, the surgeon may use outer housing 435 as a hand hold when installing and/or positioning the vibrating prosthesis.

The use of discrete transfer portions (e.g., upper, central, and lower transfer assemblies) for pulse transfer assembly 405 allows a form of loose coupling between oscillation engine 410 and a secured prosthesis. In this way pulses from oscillation engine 410 are converted into a vibratory motion of the prosthesis as it is urged into the bone during operation. Some embodiments may provide a stronger coupling by directly securing one component to another, or substituting a single component for a pair of components.

Figure 8:
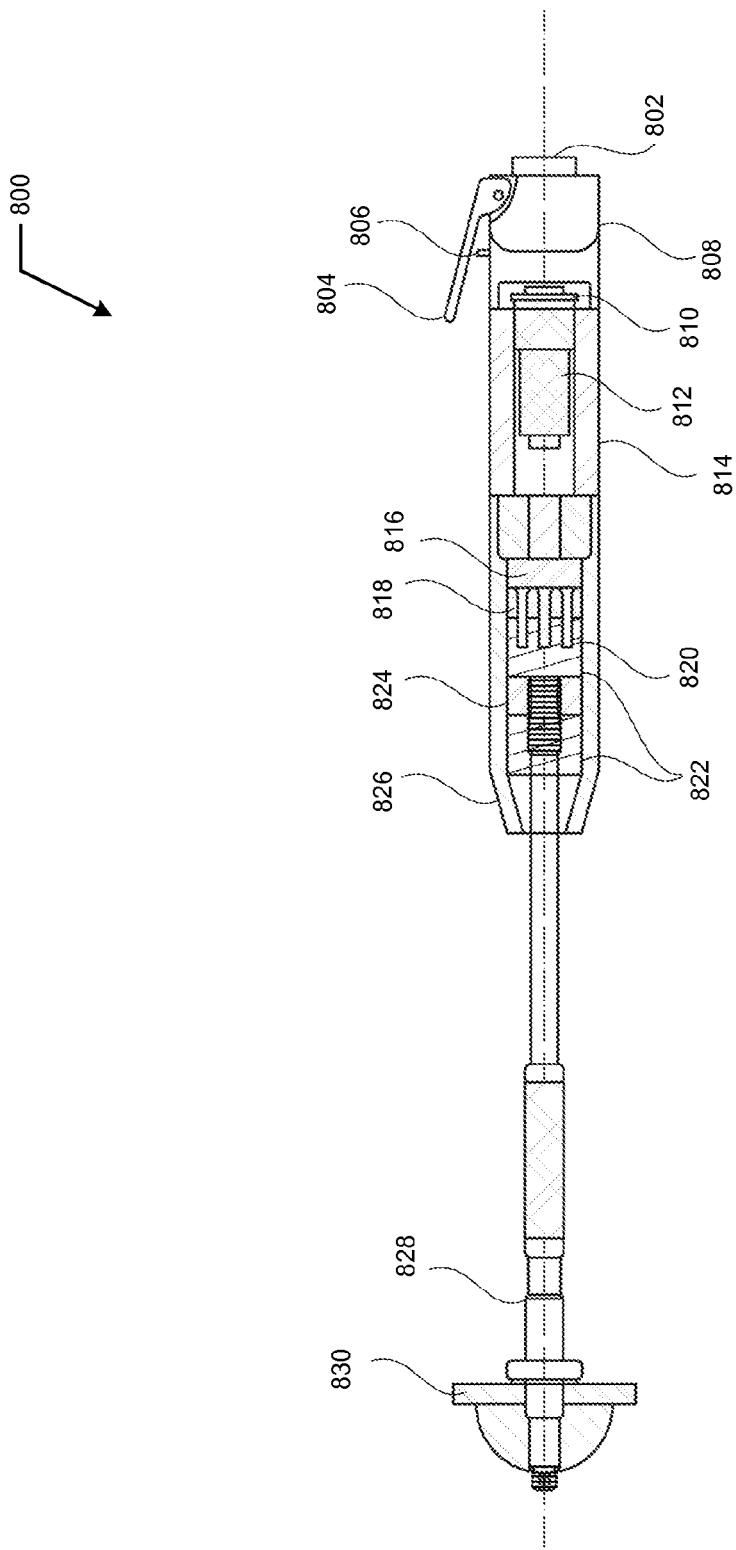
FIG. 8 illustrates a third representative installation system.
Figure 9:
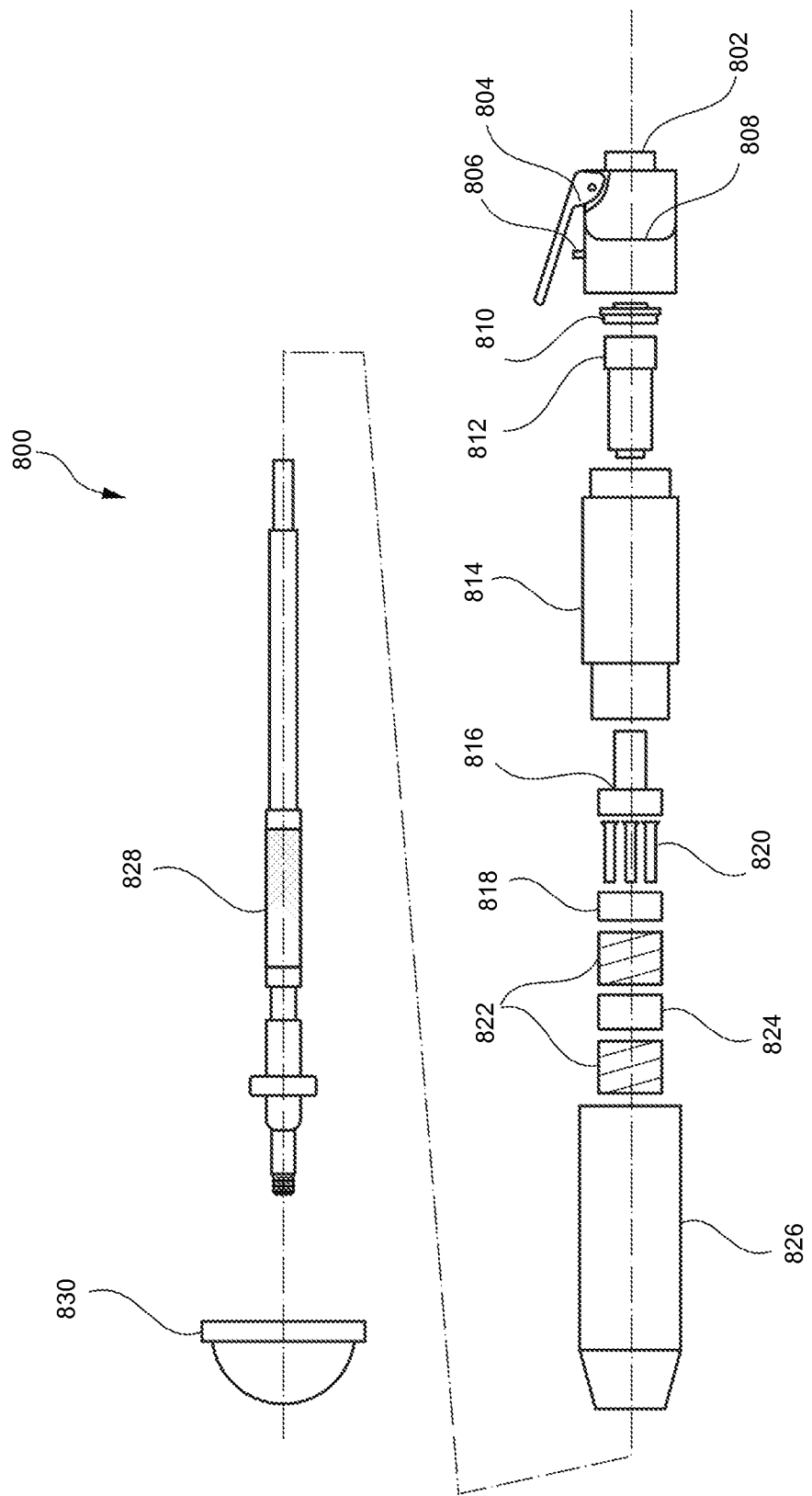
FIG. 9 illustrates a disassembly view of the third representative installation system of FIG. 8.

FIG. 8 illustrates a third representative installation system 800; and FIG. 9 illustrates a disassembly view of third representative installation system 800.

The embodiments of FIG. 4-FIG. 8 have demonstrated insertion of a prosthetic cup into a bone substitute substrate with ease and a greatly reduced force as compared to use of a mallet and tamp, especially as no impaction was required. While the insertion was taking place and vibrational motion was present at the prosthesis, the prosthesis could be positioned with relative ease by torqueing on a handle/outer housing to an exact desired alignment/position. The insertion force is variable and ranges between 20 to 800 pounds of force. Importantly the potential for use of significantly smaller forces in application of the prosthesis (in this case the acetabular prosthesis) in bone substrate with the present invention is demonstrated to be achievable.

Similarly to installation system 100 and installation system 400, installation system 800 is used to control precisely one or both of (i) installation and (ii) abduction and anteversion angles of a prosthetic component. Installation system 800 preferably allows both installation of an acetabular cup into an acetabulum at a desired depth and orientation of the cup for both abduction and anteversion to desired values. The following reference numbers in Table II refer to elements identified in FIG. 8-FIG. 9:

TABLE II

| Device 800 Elements | |
| --- | --- |
| 802 | Air Inlet |
| 804 | Trigger |
| 806 | Needle Valve |
| 808 | Valve Body |
| 810 | Throttle Cap |
| 812 | Piston |
| 814 | Cylinder |
| 816 | Driver |
| 818 | Needle Block |
| 820 | Needles |
| 822 | Suspension Springs |
| 824 | Anvil |
| 826 | Nozzle |
| 828 | Connector Rod |
| 830 | Prosthesis (e.g., acetabular cup) |

Installation system 800 includes a controller with a handle supporting an elongate rod that terminates in a connector system that engages prosthesis 830. Operation of trigger 804 initiates a motion of the elongate rod. This motion is referred to herein as an installation force and/or installation motion that is much less than the impact force used in a conventional replacement process. An exterior housing allows the operator to hold and position prosthesis 830 while the elongate rod moves within. Some embodiments may include a handle or other grip in addition to or in lieu of the housing that allows the surgeon operator to hold and operate installation system 800 without interfering with the mechanism that provides a direct transfer of installation motion. The illustrated embodiment includes prosthesis 830 held securely allowing a tilting and/or rotation of installation system about any axis to be reflected in the position/orientation of the secured prosthesis.

The actuator is pneumatically operated oscillation device that provides the impact and vibration action this device uses to set the socket (it being understand that alternative motive systems may be used in addition to, or alternatively to, a pneumatic system). Alternatives including mechanical and/or electromechanical systems, motors, and/or engines. The actuator includes air inlet port 802, trigger 804, needle valve 806, cylinder 814, and piston 812.

Air is introduced through inlet port 802 and as trigger 804 is squeezed needle valve 806 admits air into the cylinder 814 pushing piston 812 to an opposing end of cylinder 814. At the opposite end piston 812 opens a port allowing the air to be admitted and pushing the piston 812 back to the original position.

This action provides the motive power for operation of the device and functions in this embodiment at up to 70 Hz. The frequency can be adjusted by trigger 804 and an available air pressure at air inlet port 802.

As piston 812 impacts driver 816, driver 816 impacts needles 820 of needle block 818. Needles 820 strike anvil 824 which is directly connected to prosthesis 830 via connecting rod 828.

Suspension springs 822 provide a flexibility to apply more or less total force. This flexibility allows force to be applied equally around prosthesis 830 or more force to one side of prosthesis 830 in order to locate prosthesis 830 at an optimum/desired orientation. Installation system 800 illustrates a BMD having a more strongly coupled pulse transfer system between an oscillation engine and prosthesis 830.

The nature and type of coupling of pulse communications between the oscillation engine and the prosthesis may be varied in several different ways. For example, in some implementations, needles 820 of needle block 818 are independently moveable and respond differently to piston 812 motion. In other implementations, the needles may be fused together or otherwise integrated together, while in other implementations needles 820 and needle block 818 may be replaced by an alternative cylinder structure.

As illustrated, while both embodiments provide for a primarily longitudinal implementation, installation system 800 includes a design feature intended to allow the inserting/vibratory force to be "steered" by applying forces to be concentrated on one side or another of the prosthesis. Implementations that produce a randomized vibrational motion, including "lateral" motion components in addition to, or in lieu of, the primarily longitudinal vibrational motion of the disclosed embodiments may be helpful for installation of prosthesis in a wide range of applications including THR surgery.

Installation system 400 and installation system 800 included an oscillation engine producing pulses at approximately 60 Hz. System 400 operated at 60 Hz while system 800 was capable of operating at 48 to 68 Hz. In testing, approximately 4 seconds of operation resulted in a desired insertion and alignment of the prosthesis (meaning about 240 cycles of the oscillation engine). Conventional surgery using a mallet striking a tamp to impact the cup into place is generally complete after 10 blows of the mallet/hammer.

EXPERIMENTAL

Both system 400 and system 800 were tested in a bone substitute substrate with a standard Zimmer acetabular cup using standard technique of under reaming a prepared surface by 1 mm and inserting a cup that was one millimeter larger. The substrate was chosen as the best option available to us to study this concept, namely a dense foam material. It was recognized that certain properties of bone would not be represented here (e.g. an ability of the substrate to stretch before failure).

Both versions demonstrated easy insertion and positioning of the prosthetic cup within the chosen substrate. We were able to move the cup in the substrate with relative ease. There was no requirement for a mallet or hammer for application of a large impact. These experiments demonstrated that the prosthetic cups could be inserted in bone substitute substrates with significantly less force and more control than what could be done with blows of a hammer or mallet. We surmise that the same phenomena can be reproduced in human bone. We envision the prosthetic cup being inserted with ease with very little force.

Additionally we believe that simultaneously, while the cup is being inserted, the position of the cup can be adjusted under direct visualization with any intra-operative measurement system (navigation, fluoroscopy, etc.). This invention provides a system that allows insertion of a prosthetic component with NON-traumatic force (insertion)) as opposed to traumatic force (impaction).

Experimental Configuration

System 400

Oscillation engine 410 included a Craftsman G2 Hammerhead nailer used to drive fairly large framing nails into wood in confined spaces by applying a series of small impacts very rapidly in contrast to application of few large impacts.

The bone substitute was 15 pound density urethane foam to represent the pelvic acetabulum. It was shaped with a standard cutting tool commonly used to clean up a patient's damaged acetabulum. A 54 mm cup and a 53 mm cutter were used in testing.

In one test, the cup was inserted using a mallet and tamp, with impaction complete after 7 strikes. Re-orientation of the cup was required by further strikes on an periphery of the cup after impaction to achieve a desired orientation. It was qualitatively determined that the feel and insertion were consistent with impaction into bone.

An embodiment of system 400 was used in lieu of the mallet and tamp method. Several insertions were performed, with the insertions found to be much more gradual; allowing the cup to be guided into position (depth and orientation during insertion). Final corrective positioning is easily achievable using lateral hand pressure to rotate the cup within the substrate while power was applied to the oscillation engine.

Further testing using the sensor included general static load detection done to determine the static (non-impact) load to push the cup into the prepared socket model. This provided a baseline for comparison to the impact load testing. The prosthesis was provided above a prepared socket with a screw mounted to the cup to transmit a force applied from a bench vise. The handle of the vice was turned to apply an even force to compress the cup into the socket until the cup was fully seated. The cup began to move into the socket at about an insertion force of ~200 pounds and gradually increased as diameter of cup inserted into socket increased to a maximum of 375 pounds which remained constant until the cup was fully seated.

Installation system 400 was next used to install the cup into a similarly prepared socket. Five tests were done, using different frame rates and setup procedures, to determine how to get the most meaningful results. All tests used a 54 mm acetabular Cup. The oscillation engine ran at an indicated 60 impacts/second. The first two tests were done at 2,000 frames/second, which wasn't fast enough to capture all the impact events, but helped with designing the proper setup. Test 3 used the oscillation engine in an already used socket, 4,000 frames per second. Test 4 used the oscillation engine in an unused foam socket at 53 mm, 4,000 frames per second.

Test 3: In already compacted socket, the cup was pulsed using the oscillation engine and the pulse transfer assembly. Recorded strikes between 500 and 800 lbs, with an average recorded pulse duration 0.8 ms.

Test 4: Into an unused 53 mm socket, the cup was pulsed using the oscillation engine and the pulse transfer assembly. Recorded impacts between 250 and 800 lbs, and an average recorded pulse duration 0.8 ms. Insertion completed in 3.37 seconds, 202 impact hits.

Test 5: Into an unused 53 mm socket, the cup was inserted with standard hammer (for reference). Recorded impacts between 500 and 800 lbs, and an average recorded pulse duration 22.0 ms. Insertion completed in 4 seconds using 10 impact hits for a total pressure time of 220 ms. This test was performed rapidly to complete it in 5 seconds for good comparability with tests 3 and 4 used 240 hits in 4 seconds, with a single hit duration of 0.8 ms, for a total pressure time of 192 ms.

In non-rigorous comparison testing without a direct comparison between system 400 and system 800, generally it appears that the forces used for installation using system 800 were lower than system 400 by a factor of 10. This suggests that there are certain optimizing characteristics for operation of an installation system. There are questions such as to how low these forces can be modulated and still allow easy insertion of the prosthetic cup in this model and in bone. What is the lowest force required for insertion of a prosthetic cup in to this substrate using the disclosed concepts? What is the lowest force required for insertion of a prosthetic cup into hard bone using the these concepts? And what is the lowest force required for insertion of a prosthetic cup into soft and osteoporotic bone using these concepts? These are the questions that can be addressed in future phase of implementations of the present invention.

Additionally, basic studies can further be conducted to correlate a density and a porosity of bone at various ages (e.g., through a cadaver study) with an appropriate force range and vibratory motion pattern required to insert a cup using the present invention. For example a surgeon will be able to insert sensing equipment in patient bone, or use other evaluative procedures, (preoperative planning or while performing the procedure for example) to asses porosity and density of bone. Once known, the density or other bone characteristic is used to set an appropriate vibratory pattern including a force range on an installation system, and thus use a minimal required force to insert and/or position the prosthesis.

BMD is a "must have" device for all medical device companies and surgeons. Without BMD the Implantation problem is not addressed, regardless of the recent advances in technologies in hip replacement surgery (i.e.; Navigation, Fluoroscopy, MAKO/robotics, accelerometers/gyro meters, etc.). Acetabular component (cup) positioning remains the biggest problem in hip replacement surgery. Implantation is the final step where error is introduced into the system and heretofore no attention has been brought to this problem. Current technologies have brought significant awareness to the position of the implants within the pelvis during surgery, prior to impaction. However, these techniques do not assist in the final step of implantation.

In FIG. 1-FIG. 9, and the discussion above, BMD embodiments addressing various installation implementations (including installation and positioning) have been illustrated and described. In many of the disclosed embodiments, there is no requirement for post-installation positioning of the prosthesis as the prosthesis is precisely inserted and aligned as desired.

In FIG. 10-FIG. 34 there are illustrated a set of systems and methods to address prosthesis mal-alignment AFTER the prosthesis has been implanted without attendant correct alignment irrespective of the system or method that has implanted the prosthesis. As noted herein, some implementations of the systems and methods disclosed with respect to FIG. 1-FIG. 9 may also be used to "float" a previously installed prosthesis to allow correct positioning, such as may be the case where a decision is made to change a desired alignment for the installed prosthesis. Float, in this context for the purposes of this invention refers to removal and/or reduction of forces inhibiting a re-orienting of an inserted and mispositioned prosthesis (e.g., static frictional forces) to allow the surgeon to properly orient the prosthesis.

The systems of methods of FIG. 12-FIG. 34 when realized as a positioning BMD were conceptualized and intended to be used with the navigational systems that provide real time information during the surgical procedure such as those now available; as well as other variety of real-time monitoring systems such as (fluoroscopy and accelerometers/gyrometers).

Figure 10:
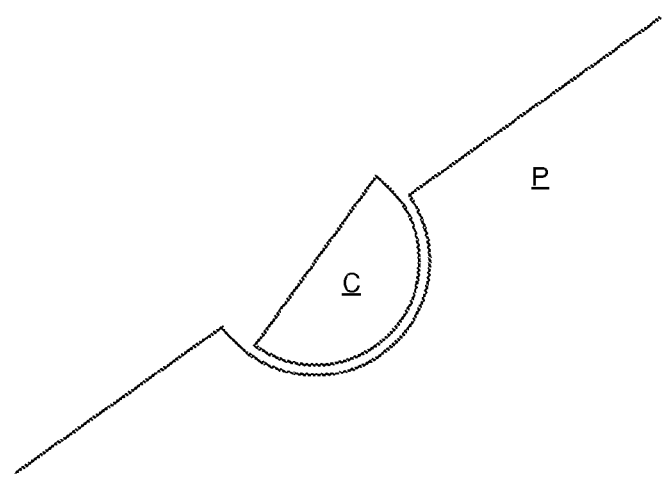
FIG. 10 illustrates a schematic side section representation of an acetabular cup mispositioned into a pelvis.
Figure 11:
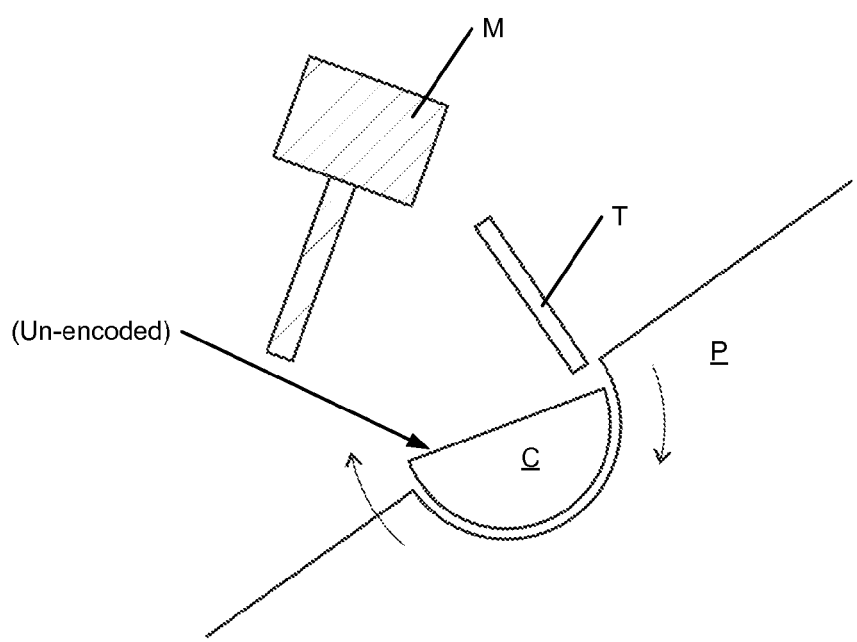
FIG. 11 illustrates a conventional use of a mallet and tamp to apply an orientation-altering force to an unencoded and mispositioned acetabular cup, such as that illustrated in FIG. 10.

FIG. 10 illustrates a schematic side section representation of an acetabular cup C mispositioned into a portion of a pelvis P. Misposition, in this context, refers to an inserted prosthesis that has a preferred orientation before attaining that preferred orientation. FIG. 11 illustrates a conventional use of a mallet M and tamp T to apply an orientation-altering force to an unencoded and mispositioned acetabular cup C, such as that illustrated in FIG. 10. Typically, no matter how well the position of the patient's pelvis, the operating room table, and the prosthetic components are monitored in surgery (navigation), during the implantation process, cup C ends up in a less than desired position (i.e., mispositioned). This condition often occurs due to a lack of control of the forces created by the uneven blows of mallet M on impacting tamp T. Currently, when a surgeon desires to change the alignment of an already impacted cup C, various locations on an edge of cup C are struck using tamp T and mallet M.

A problem with this solution is that the surgeon has no a priori idea how any particular impact on the cup will change the specific alignment of cup C. For example, while the surgeon knows that when a general part of cup C is tamped (e.g., a "front") this will change varying degrees of anteversion, this action will also inadvertently produce some unwanted change amount of abduction or adduction depending on where this impact was made (above or below the equator). It is quite accurate to state that when the surgeon uses tamp T and mallet M to correct the position of an already implanted cup C, that the surgeon does not know precisely the location and direction to achieve the desired orientation with complete precision.

Positioning BMDs are a result of an insight/invention devised to provide a solution to this particular problem: How the surgeon correct the misposition of an already implanted cup C with some measure of accuracy? The goals here were to (1) provide a map or a way to use current technology to define, quantify, digitize, and encode an already implanted prosthetic cup C; and (2) to provide a tool that could produce measurable, reliable, and predictable changes to the position of cup C.

Figure 12:
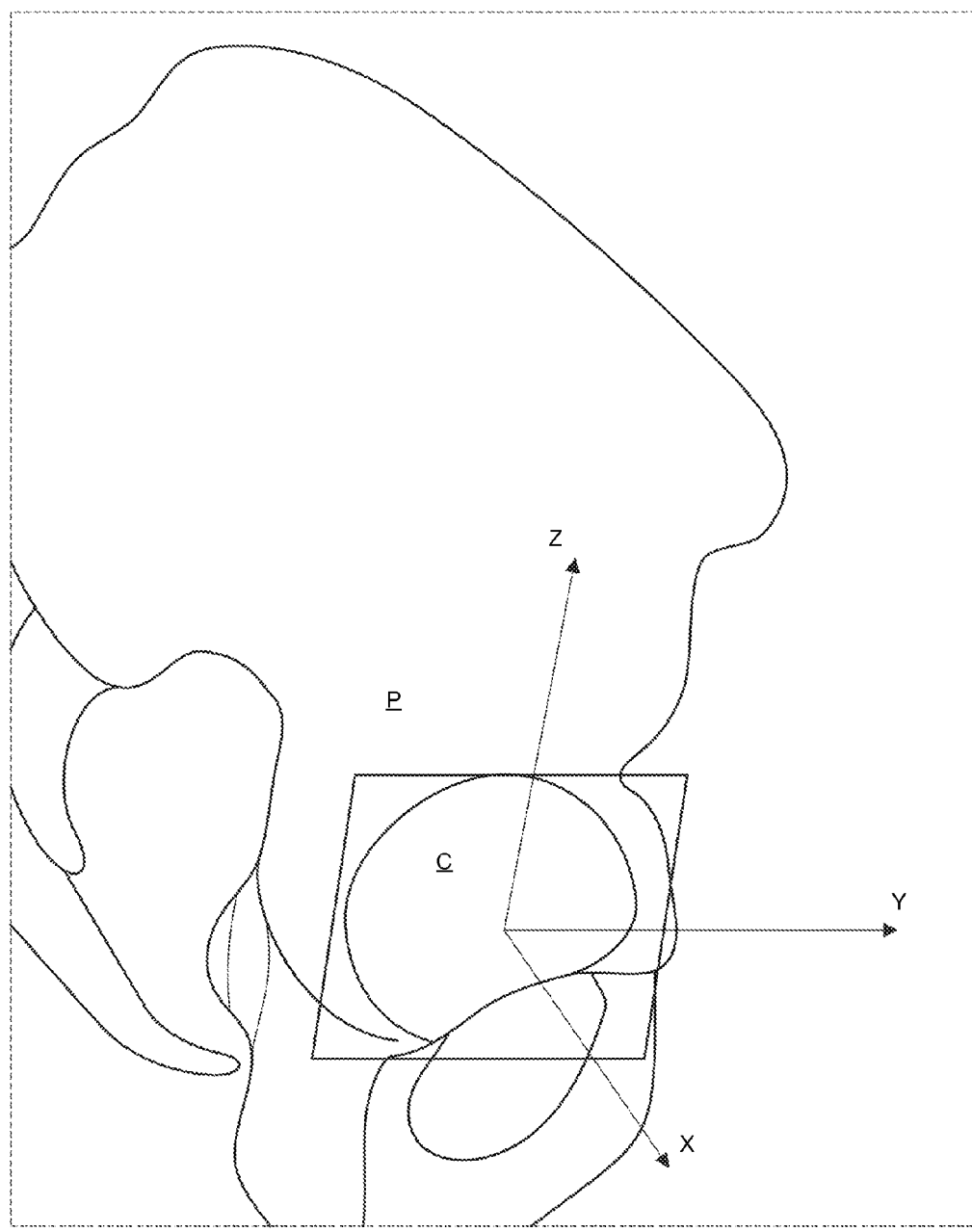
FIG. 12-FIG. 14 illustrate a reference frame used in THR surgery including an acetabular prosthesis installed into a pelvis including identified orthogonal axes.
Figure 13:
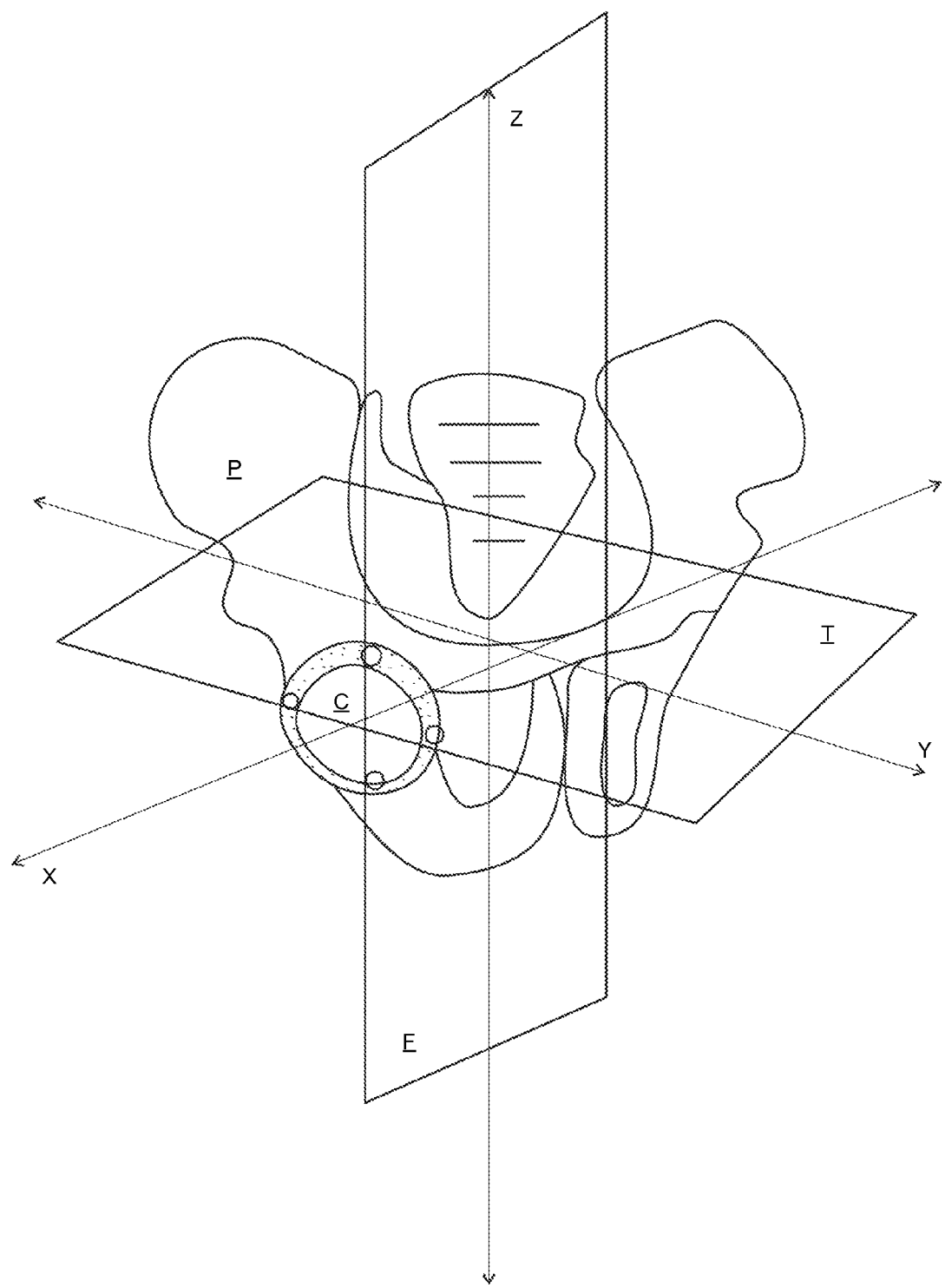
Figure 14:
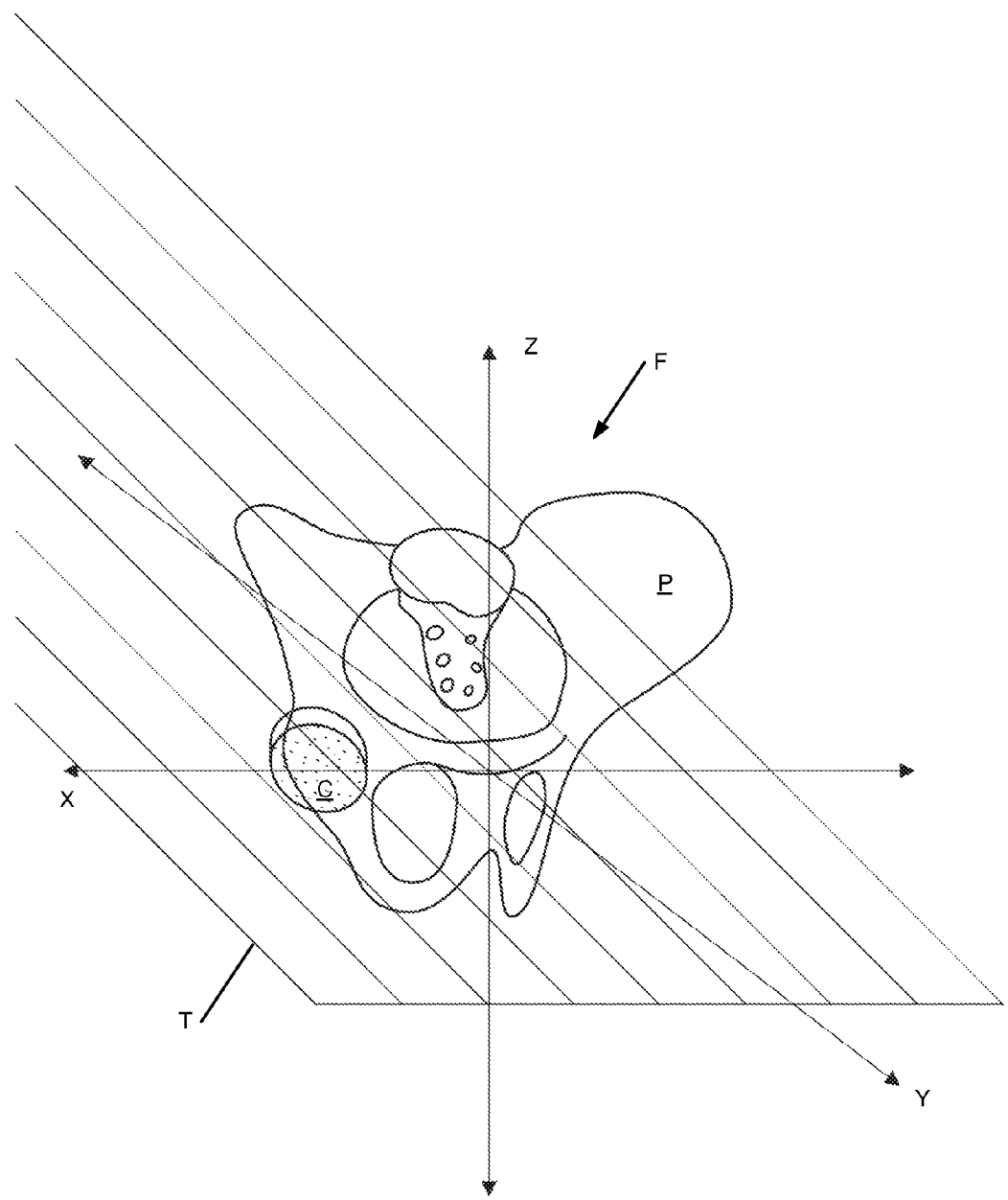

FIG. 12-FIG. 14 illustrate a reference frame used in THR surgery including an acetabular prosthesis (e.g., cup C) installed into a pelvis P including identified X-Y-Z orthogonal axes. FIG. 12 illustrates the reference frame and the orthogonal axes; FIG. 13 illustrates the orthogonal axes with an associated frontal plane F and a transverse plane T; and FIG. 14 illustrates a different perspective view of the orthogonal axes with the associated frontal plane F and transverse plane T.

In an operating room employing a navigation system, the reference frame is established in which the location of the patient on the operating room table is mapped. Frontal plane F and transverse plane T are set to pass through the acetabulum and, consequently, the inserted cup C. It is with respect to this reference frame that any particular desired orientation (e.g., a particular amount or range of abduction and anteversion). In conventional procedures, a range is typically specified because of challenges in achieving a particular amount. In some implementations, a different reference frame may be used, however there will typically be a way to remap such a different reference frame to the reference frame described herein.

Pure Points:

Pure Points on the implanted cup are determined using mathematical calculations within the reference frame as defined below. Given facts: Frontal plane F is constructed by the X and Z axis and transverse plane T is constructed by the X and Y axis.

A pure abduction point on an edge of an inserted acetabular cup is a spot defined by a highest point on frontal plane F on the positive side of the Z-axis when the cup is transposed on frontal plane F.

A pure adduction point on the edge of the cup is a spot defined by the lowest point on frontal plane F on the negative side of the Z-axis, when the cup is transposed on frontal plane F.

A pure anteversion point on the edge of the cup is a spot defined by the highest point on the Y-axis of transverse plane T in the positive direction.

A pure retroversion point on the edge of the cup is a spot defined by the lowest point on the Y-axis of transverse plane T in the negative direction.

These pure points were conceived to create a map of the edge of an installed cup for use with a positioning BMD system or tool. Once these four essential points are defined and encoded (actual and/or virtual encoding) on the edge of the cup with navigation software, the additional points in between can be quantified with trigonometric calculations. Virtual encoding in this context refers to determination and mapping of the pure points in the reference frame for an installed cup and does not require any tangible indicia to be applied. In some implementations of the present invention, there may be ways to directly communicate these pure points to the surgeon in real-time such as by various visual cues. Other implementations may provide indirect communication of the pure points during use and operation of the systems and methods.

Figure 15:
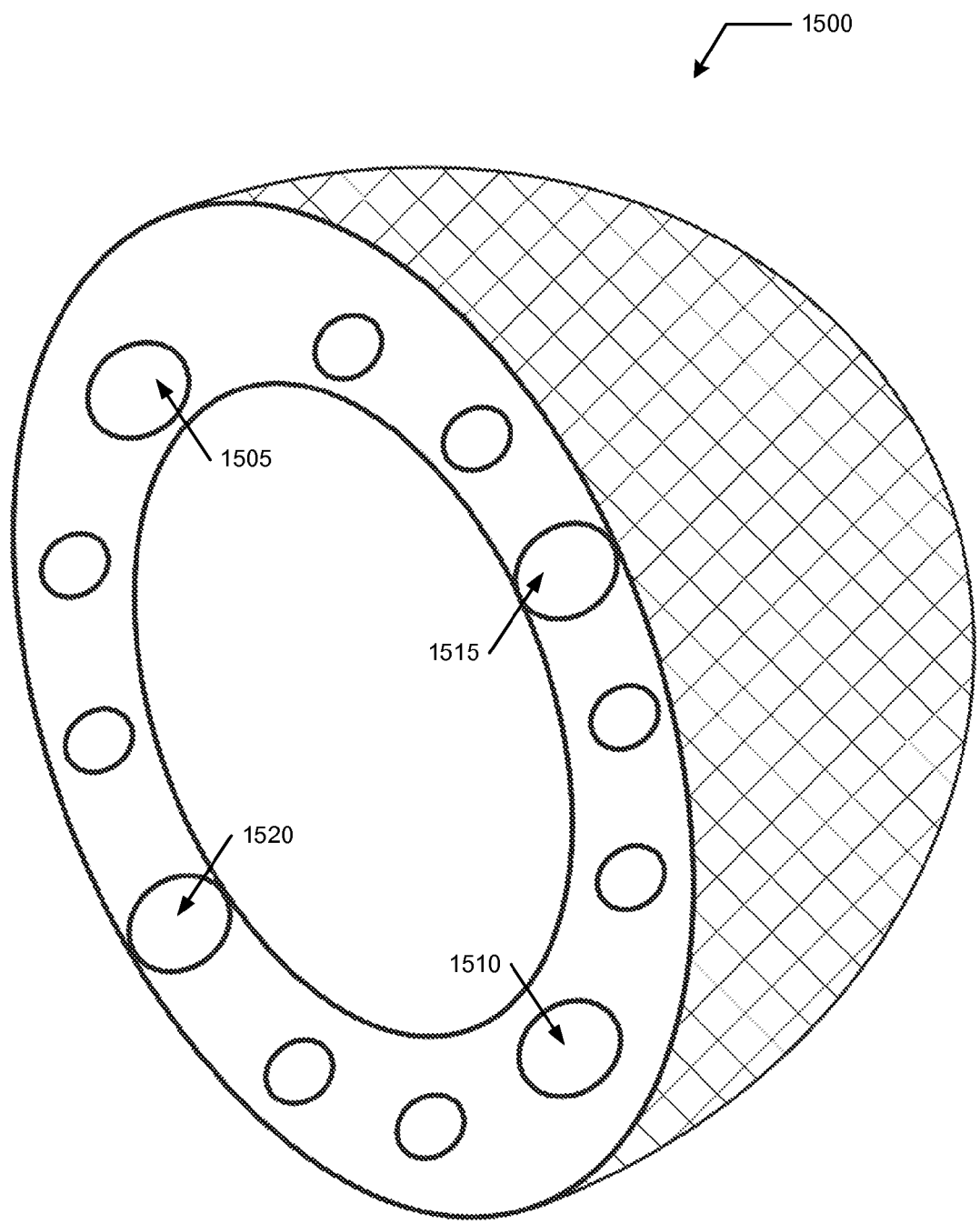
FIG. 15 illustrates an encoded prosthesis including a set of pure points.

FIG. 15 illustrates an encoded prosthesis 1500 including a set of pure points. This set includes: a pure adduction point 1505, a pure abduction point 1510, a pure anteversion point 1515, and a pure retroversion point 1520. Intermediate points between adjacent pure points produce some amount of both associated points, as may be determined from trigonometric calculations.

Figure 16:
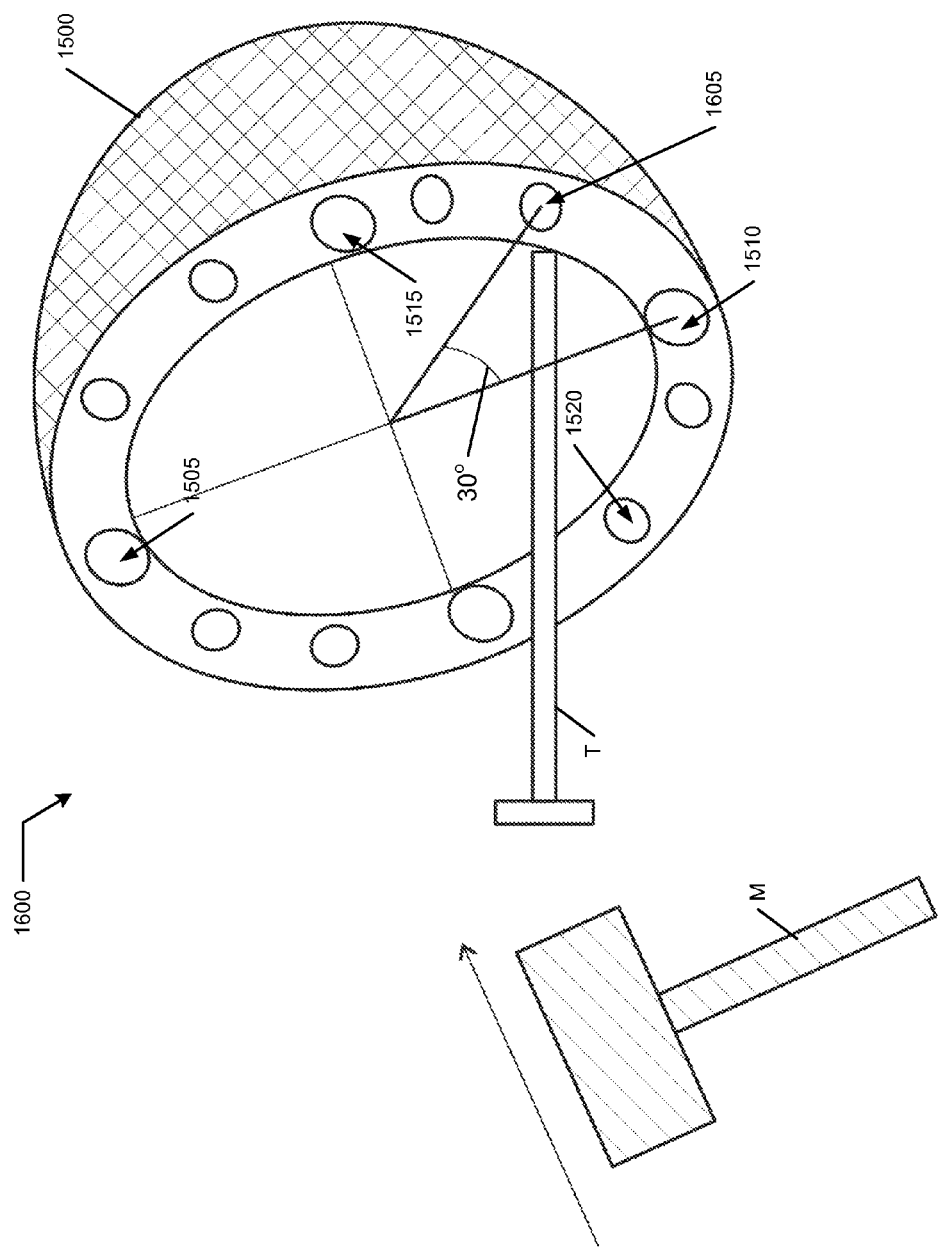
FIG. 16 illustrates a positioning of an encoded prosthesis.

FIG. 16 illustrates a manual positioning system 1600 for encoded prosthesis 1500 using mallet M and tamp T. The edge of cup 1500 is now encoded with information (i.e., it is digitized and quantified in the reference frame). The surgeon now has a type of map and sense of how to manipulate an inserted and mispositioned encoded cup 1500 to produce the desired orientation. The surgeon knows the pure points and understands that any impact on an edge of cup 1500 between pure abduction and pure anteversion (e.g., 30 degrees in front of pure abduction 1605) will produce both abduction and anteversion motion. Based on trigonometric calculations, the surgeon now anticipates a higher increase in abduction than anteversion. The contribution of impacted force towards each of these planes can now be quantified allowing the surgeon to accurately, precisely, efficiently, and predictably achieve a specific desired orientation.

Figure 17:
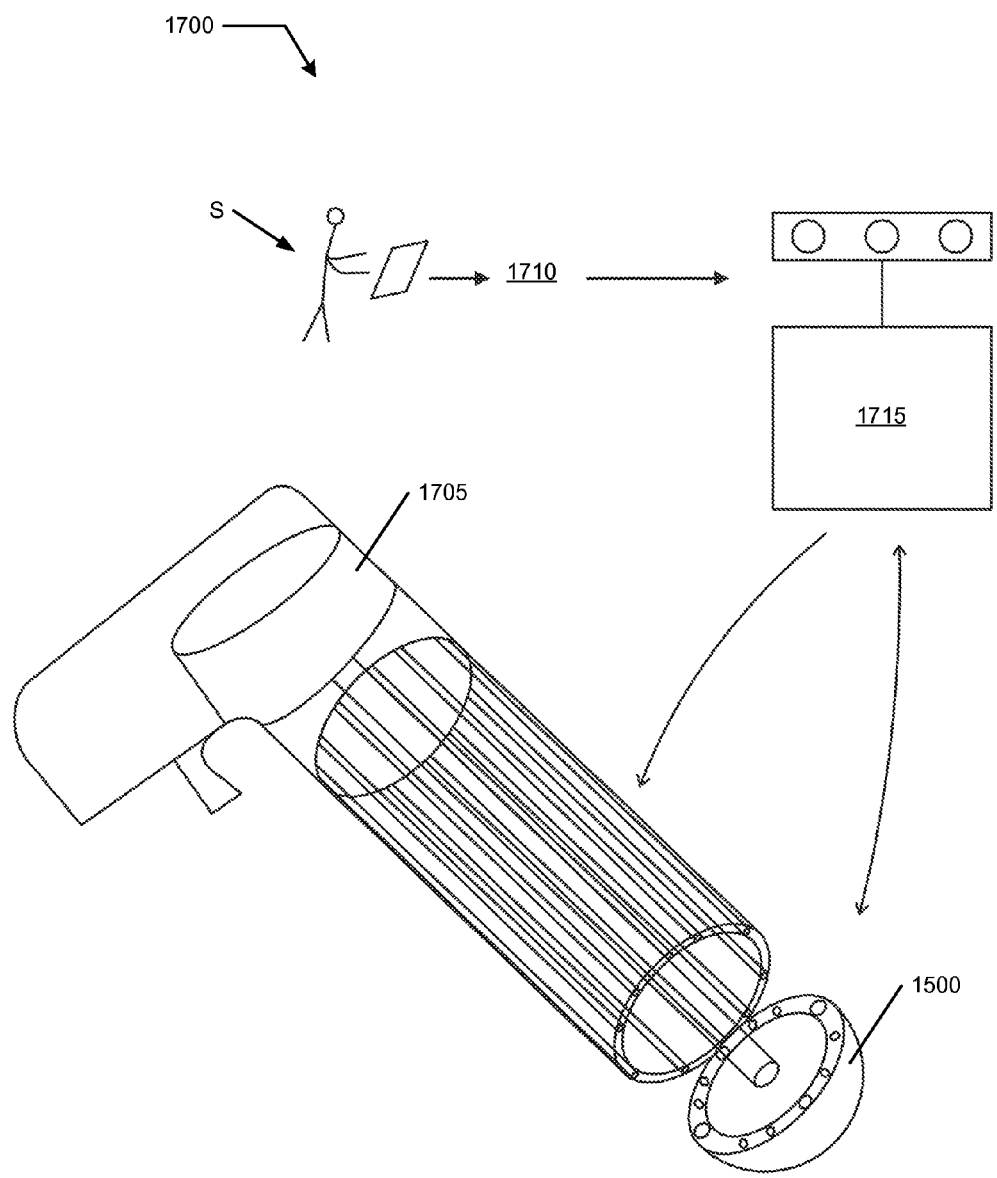
FIG. 17 illustrates an automated positioning of an encoded prosthesis.

FIG. 17 illustrates a positioning system 1700 having a positioning BMD 1705 orient an inserted and mispositioned encoded prosthesis 1500. Positioning BMD 1705 was conceived as a tool that a surgeon S would apply it to an already implanted cup, and simply "dial in" a desired alignment 1710. A purely automated positioning BMD incorporated into a computer navigation system 1715 would do the rest, correcting a position of an inserted and mispositioned cup to the desired alignment, (essentially completely automating this corrective process, eliminating surgeon error and unpredictability). An early positioning BMD, represented by positioning BMD 1705 includes twelve actuators evenly distributed around a 360 degree cup periphery (each actuator thus separated by 30 degrees around the edge of the cup).

BMD 1705, in cooperation with encoded cup 1500 and the above described additions to the navigation software, surgeon S now proceeds with a digitized and "encoded" cup (pure points on the cup's edge are defined in by the reference frame in the operating room space). Surgeon S proximates (i.e., attaches, contacts, or otherwise uses BMD 1705 to control an orientation of cup 1500) positioning BMD 1705 to inserted cup 1500, such as with an adaptor specific to this prosthesis as BMD 1705 may be used in some cases for other prostheses), and dials in the desired alignment 1710 for cup 1500 (for this example, 40 degrees abduction and 20 degrees anteversion is desired with the inserted and malpositioned cup initially at 50 degrees abduction and 30 degrees anteversion). Computer navigation system 1715 then calculates the point on the cup that is most likely to produce the desired change as any force impacted on the cup now produces a predictable increase/decrease in abduction/anteversion which is now quantified by navigation system 1715. Navigation system 1715 then chooses an actuator of BMD 1705 that corresponds to that point on the cup, impacting on that calculated point. After the corrective impact, a re-measurement of the cup's position would have to be done and made available to navigation system 1715 so that the new position is known. The cup has now a new alignment. This process is repeated until the desired alignment of the implanted cup is achieved. Computer navigation system 1715 continues this process through a feedback loop mechanism until the position of the cup is exactly the same as that which was dialed in by surgeon S.

Figure 18:
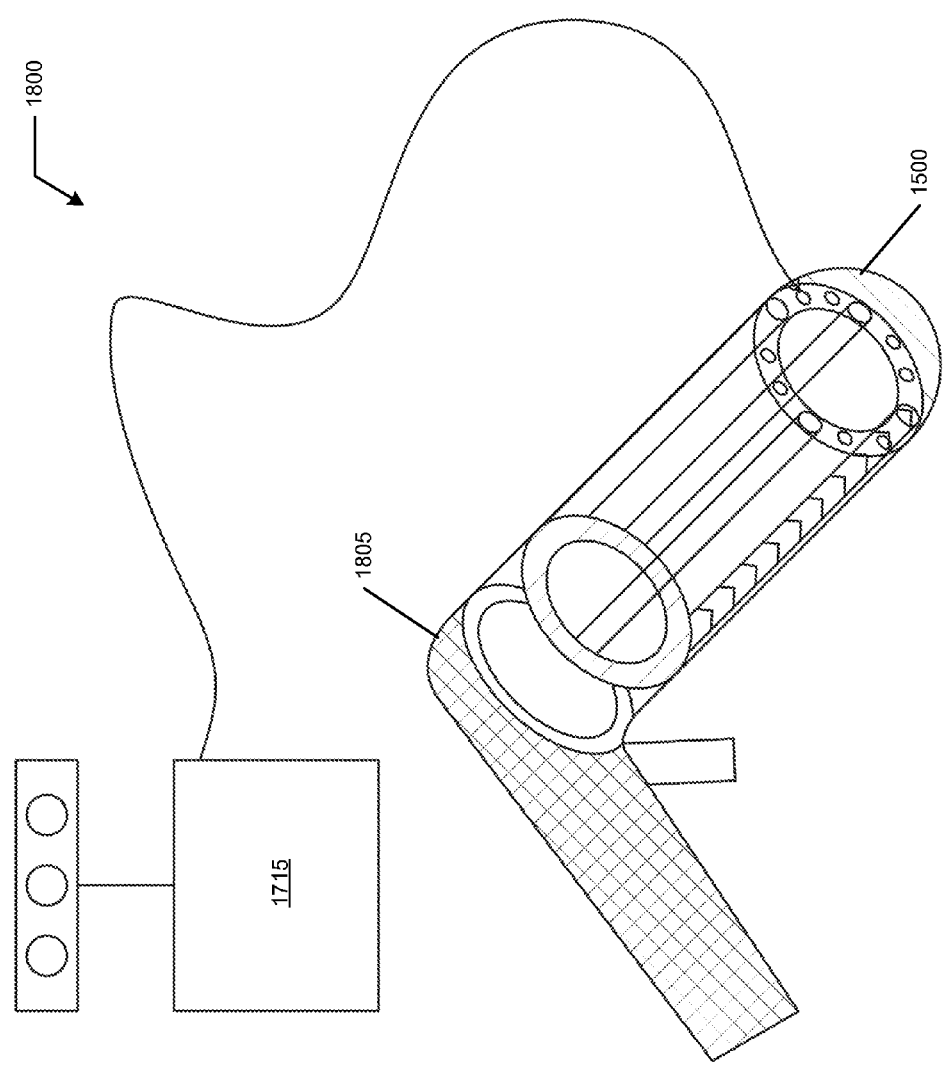
FIG. 18 illustrates a schematic representation of an embodiment of a positioning gun configured for prosthesis adjustment.

FIG. 18 illustrates a schematic representation of an embodiment of positioning system 1800 using a positioning BMD 1805 configured for correcting inserted and malpositioned prostheses. While system 1700 was conceived as a purely automated optimal solution, other systems may also be implemented that include some manual and/or semi-automated steps. System 1700 was created to eliminate surgeon error, automate the process of cup implantation, relieve surgeon anxiety and reassure patients that a better and more comprehensive system is available for the procedure of total hip replacement surgery. With system 1700, regardless of surgeon experience a "perfect cup placement" could be achieved. Regardless of which hospital a patient elected for the THR procedures, the patient would leave having "a perfect cup" result. This idea was developed to eliminate the problem of hip dislocations, wear, impingement, readmissions and reoperations and waste.

System 1800 is a simpler implementation using a different embodiment for positioning BMD 1805 that includes four orthogonal actuators that surgeon S may align with the pure points. Surgeon S could then manually direct and individually fire the actuators to change the cup alignment to achieve the desired result with computer navigation system 1715 providing results of each intermediate operation.

Figure 19:
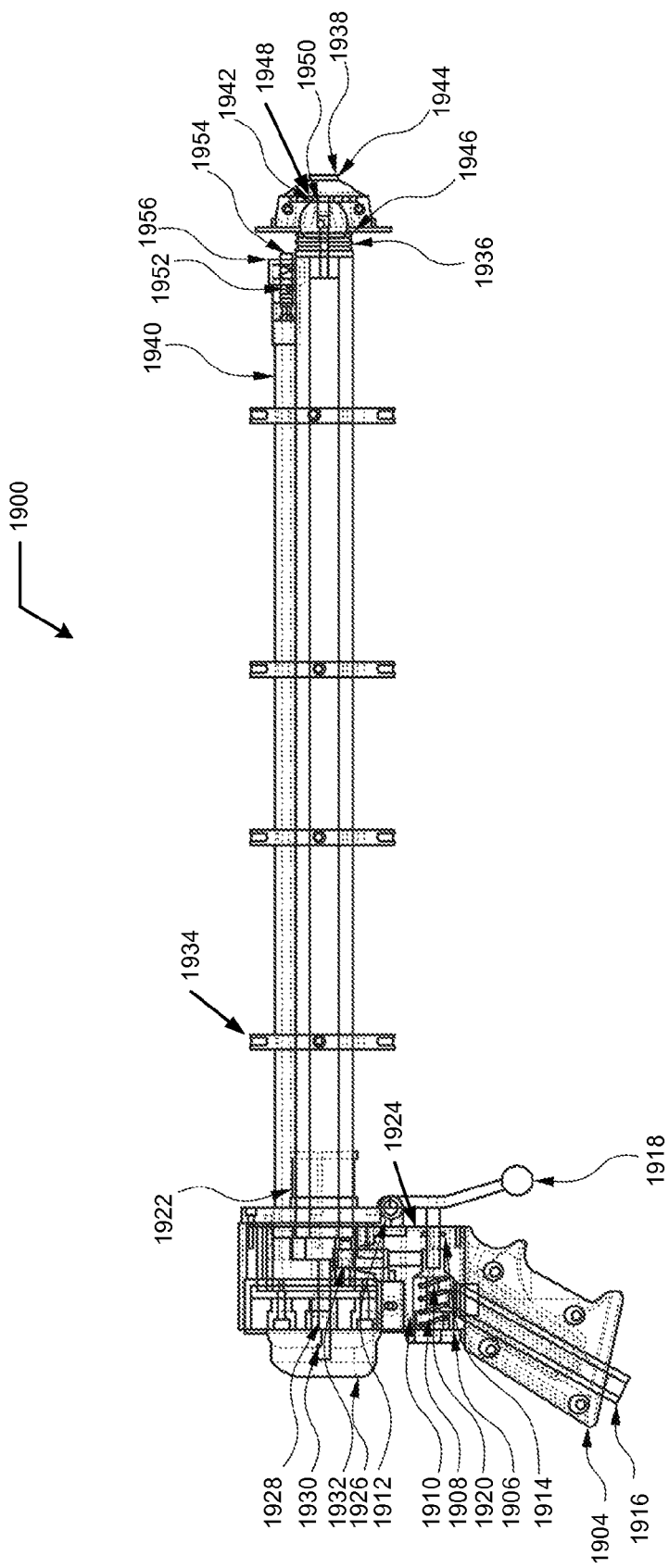
FIG. 19-FIG. 21 illustrate a detailed schematic of an embodiment of a positioning gun configured for prosthesis adjustment.
Figure 20:
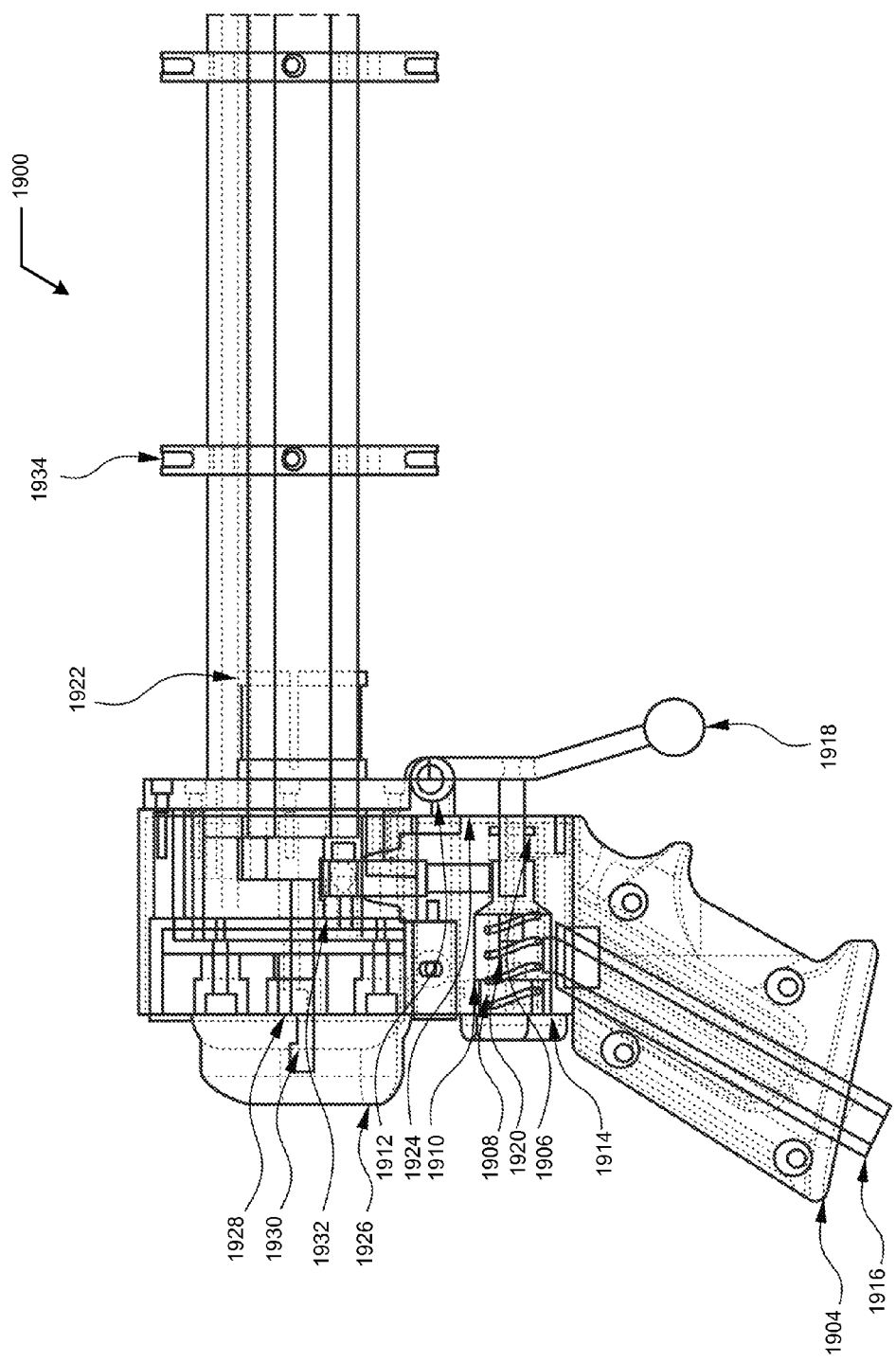
Figure 21:
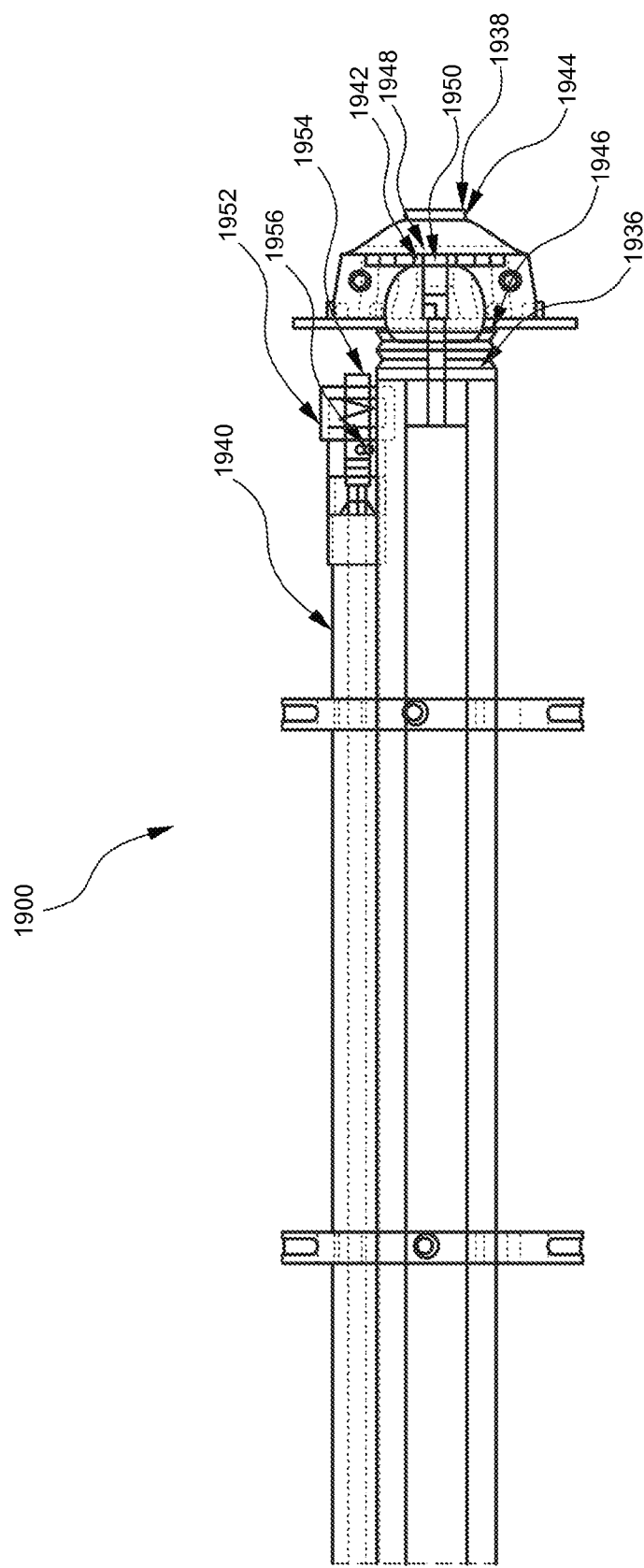

FIG. 19-FIG. 21 illustrate a detailed schematic of an embodiment of a positioning gun 1900 configured for prosthesis adjustment which is an implementation of BMD 1805. FIG. 19 illustrates a representative positioning gun 1900; FIG. 20 illustrates a left-hand detail of positioning gun 1900; and FIG. 21 illustrates a right-hand detail of positioning gun 1900 and generally when combined with FIG. 20 produces the illustration of FIG. 19.

Positioning gun 1900 is used to control precisely abduction and anteversion angles of a prosthetic component, in this case, an acetabular cup installed into an acetabulum. The following reference numbers in Table III refers to elements identified in FIG. 19-FIG. 21:

TABLE III

Device 1900 Elements

| | |
|---|---|
| 1902 | Acetabular cup (not shown) |
| 1904 | Hand grip |
| 1906 | Body |
| 1908 | Valve |
| 1910 | Bottom Cap |
| 1912 | Handle Cam |
| 1914 | DIN 3771 6 × 1,8-N-NBR 70 (O-ring) |
| 1916 | Input Tube |
| 1918 | Trigger |
| 1920 | 9657K312 |
| 1922 | Grip guide housing |
| 1924 | MirrorAR15 - Hand Grip 1 |
| 1926 | Dial Valve Body |
| 1928 | Dial Valve cap |
| 1930 | Dial Valve guide |
| 1932 | Knob |
| 1934 | Middle Guide housing |
| 1936 | Lower Guide housing |
| 1938 | Primary adapter right side |
| 1940 | Airtube |
| 1942 | Lower Guide end point |
| 1944 | Primary adapter left side |
| 1946 | 1561T480 |
| 1948 | Cup clamp |
| 1950 | Cup piston lock |
| 1952 | FINDEVA FAL 18 pneumatic knocker |
| 1954 | FINDEVA FAL 18 pneumatic knocker ram |
| 1956 | Spring cap |
| 1958 | 9657K265 |

Positioning gun 1900 essentially includes a handle/grip control for a set of elongate longitudinal actuators arranged around a central support. An adapter attached to the central support mounts to and releasably engages the prosthetic to be adjusted. This adapter allows relative motion between the central support and the cup and provides as many degrees of freedom as necessary or desirable to enable the features implemented by the device (not all implementations will include all features). This embodiment includes two degrees of freedom for rotation about each of two perpendicular axes.

In one implementation, the adapter allows appropriate freedom of motion permitting the cup to move in positive and negative anteversion and abduction angles. The set of elongate longitudinal actuators include four actuators that are equally distributed around the central support at ninety degree angles relative to each adjacent actuator. These actuators include an actuator head that strikes a portion of rim periphery of the acetabular shell to impart a controllable and variable longitudinal impact at a precise location on the edge. Preferably the four actuators are each aligned with one of the four pure anteversion and abduction points (i.e., locations where application of the longitudinal impact alters only one of anteversion or abduction).

To simplify the discussion, the controller is pneumatically or electronically powered and provides an ability to control a magnitude and/or frequency of the longitudinal actuators independent from each other. A dial on at the end of the controller may select a particular one actuator for operation in response to actuation of the trigger. The trigger results in application of the longitudinal impact at the desired point on the edge of the cup, and when implemented as described, each actuator will control only one of the four pure points so the acetabular cup will move either positive anteversion, negative anteversion, positive abduction, or negative abduction with any single actuator.

The control may be manual which includes the operator selecting a particular set of one or more actuators and triggers them for operation. The triggering causes one or more of a series of impacts to strike specific locations along the rim to adjust the angle to a desired value. The one or more impacts may have a constant or variable magnitude. Such as each trigger operation causes the set of actuators to strike the rim at the selected location(s) with a desired magnitude (that may be predetermined or adjusted by the operator). Or each trigger operation may cause a series of strikes, each with the same or different (e.g., increasing magnitude ranging between preset limits of a low value to a high value). The number of strikes may be preset or continue as long as the operator maintains the trigger operation. For example, the operator may engage the trigger and the actuator(s) continue until the trigger is released. Some implementations may include a trigger that allows the operator to control the magnitude of the impacts from the set of actuators, such as a light pull causing strikes of a certain force and a greater pull on the trigger resulting in strikes of a greater magnitude.

In some implementations, the controller includes a stored program processing system that includes a processing unit that executes instructions retrieved from memory. Those instructions could control the selection of the set of actuators and/or triggering autonomously to achieve values for abduction and anteversion entered into by the surgeon or by a computer aided medicine computing system such as the computer navigation system. Alternatively those instructions could be used to supplement manual operation to aid or suggest selection of the actuator set and/or triggering force(s) (not all actuators of a set require that they strike the rim with the same magnitude).

Thus the resulting impact(s) from operation of any single actuator of the set of selected actuators may be one or more equal strength impacts, a set of periodic impacts that continue until the trigger is released, or any other combination of constant or variable amplitude and/or frequency impacts.

As described, the four pure adjustment points are mapped out and identified in advance so that the operator may align the actuators appropriately during preparation. In some systems, it may be the case that the four points have NOT been mapped out in advance. In such circumstance, the computer navigation system may respond to a first longitudinal impact to map out the four points. After mapping, the actuators may be appropriately repositioned. In some implementations, the adapter may provide a rotational freedom of motion to allow the actuators to be rotated about a longitudinal axis of the central support so that the actuators are all appropriately aligned with the pure locations. After that, the operator may manually select a particular actuator for operation to adjust anteversion and abduction appropriately and independently.

In some implementations, it may be desirable to use feedback from the navigation system to determine how multiple simultaneous actuators all operating simultaneously on the cup can adjust the orientation to the desired anteversion and abduction. For example, when one actuator may move anteversion 2 units in the appropriate direction while also adding one undesired unit of abduction, the computer navigation system may use multiple actuators at the same time to apply the appropriate adjustment while cancelling out the undesired adjustment.

While a system employing four actuators is described above, other embodiments may include other numbers of longitudinal actuators, such as N number of actuators, N=1 to 24 actuators, most preferably evenly distributed around a periphery of the edge of acetabular cup (e.g., for 24 cups, each actuator would be 15 degrees separated from an adjacent actuator).

For more automated systems, even distribution of the actuators about the central support are not required and it may be that asymmetric arrangements better conform to an adjustment profile of the cup installed into the acetabulum. An adjustment profile is a characterization of the relative ease by which abduction and anteversion angles may be adjusted in positive and negative directions. In some situations these values may not be the same and the positioning gun could be enhanced to adjust for these differences. For example, a unit of force applied to pure positive anteversion may adjust anteversion in the positive direction by a first unit of distance while under the same conditions that unit of force applied to pure negative anteversion may adjust anteversion in the negative direction by a second unit of distance different from the first unit. And these differences may vary as a function of the magnitude of the actual angle(s). For example, as the anteversion increases it may be that the same unit of force results in a different responsive change in the actual distance adjusted. The adjustment profile when used helps the operator when selecting the actuators and the impact force(s) to be applied.

In some implementations, a constraint of system 1800 is that surgeon S wait for current orientation information of cup 1500 in between actuations of positioning BMD 1805 may discourage some surgeons from considering its use despite the many benefits for the patient, surgeon, and facility. A solution to a problem of requiring remeasurement in-between actuations could further promote adoption of embodiments of a positioning BMD. One such solution includes transferring the encoding information from the prosthesis to the positioning BMD. This paradigm allows the information, regarding the desired position of the cup, to be held and maintained on the gun, at all times, eliminating any need to re-measure the position of the cup after every corrective impact. This includes additionally mapping the encoded information of the positioning BMD into the reference frame that includes the operating room and the prosthesis.

Figure 24:
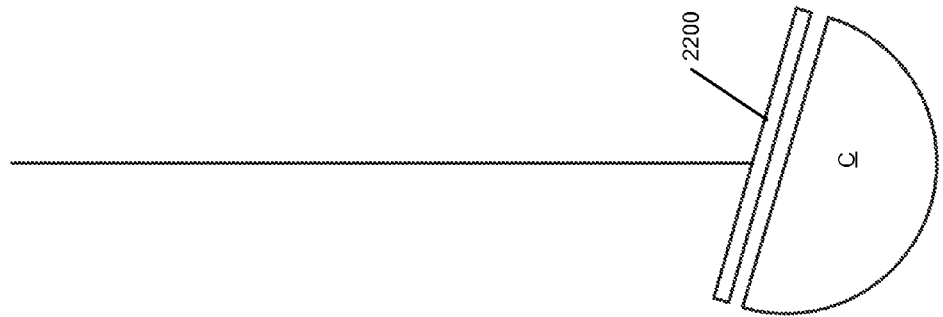
FIG. 22-FIG. 24 illustrate use of an impact ring for positioning an installed prosthesis.
Figure 23:
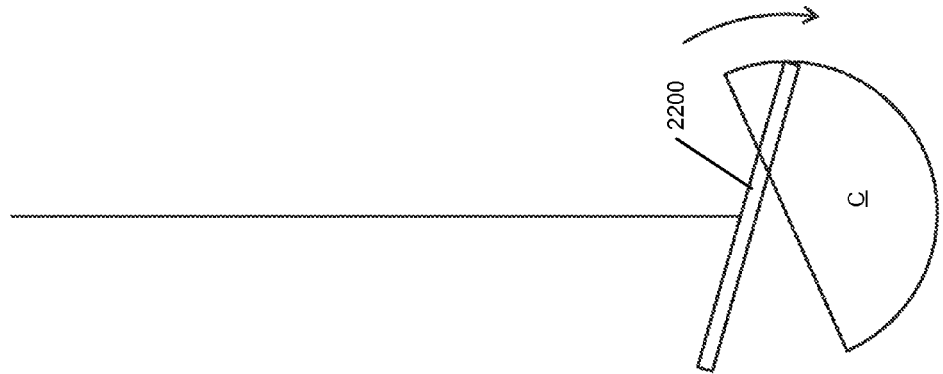
Figure 22:
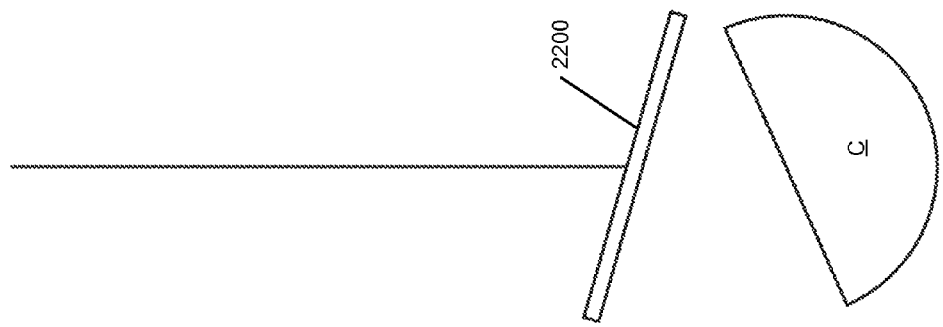

FIG. 22-FIG. 24 illustrate use of an impact ring 2200 for positioning an installed prosthesis (e.g., an acetabular cup C); FIG. 22 illustrates an initial condition of the pre-positioned installed prosthesis C with respect to impact ring 2200 installed on a positioning system; FIG. 23 illustrates an intermediate condition of the pre-positioned installed prosthesis C with respect to impact ring 2200 installed on a positioning system; and FIG. 24 illustrates a final condition having a positioned installed prosthesis C with respect to impact ring 2200 installed on a positioning system. Impact ring 2200 holds the desired orientation in the reference frame and by using a positioning BMD associated with impact ring 2200 operating on prosthesis C, the positioning BMD achieves the desired orientation when cup C conforms to the desired orientation established by impact ring 2200 as illustrated in FIG. 24.

Figure 25:
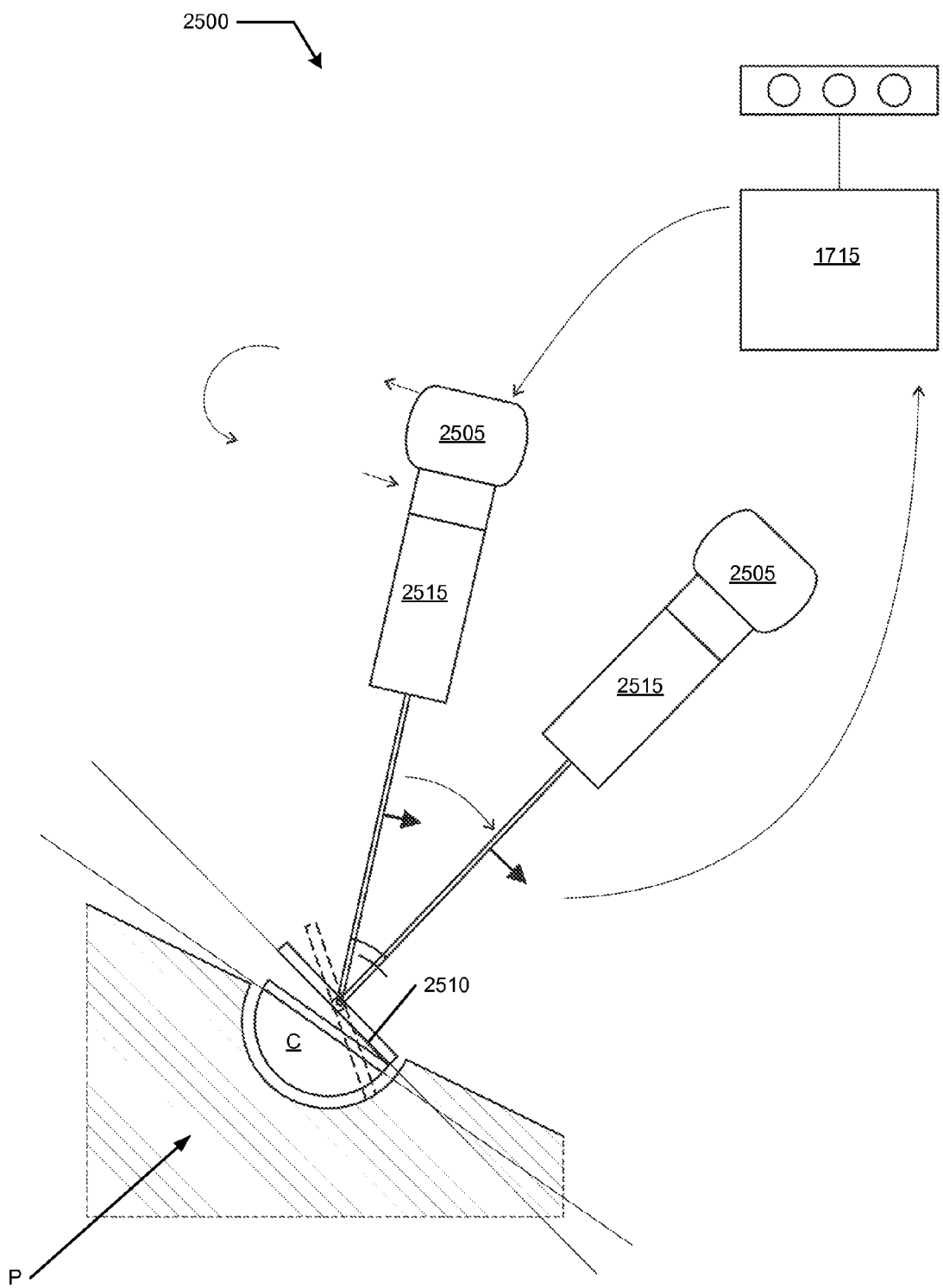
FIG. 25 illustrates an embodiment of a positioning system employing an impact ring.

FIG. 25 illustrates an embodiment of a positioning system 2500 employing a positioning BMD 2505 including an impact ring 2510. System 2500 employs computer navigation system 1715 in this case to provide information to BMD 2500 for setting impact ring 2510 to properly orient cup C in pelvis P. BMD 2505 basically transfers positional information previously encoded on the edge of the cup C using navigation system 1715 to impact ring 2510. Impact ring 2510 has an orientation relative to handle 2515 that may be adjusted (e.g., by servo motors or the like) to set a desired orientation within the reference frame of the operating room by use of navigation system 1715.

A position/plane of impact ring 2510 is measured and calibrated in the reference frame (similarly to how the plane of the implanted cup and the pelvic bone is calibrated and known in the reference frame for the non-impact ring versions of a positioning BMD). A position of the BMD 2505 axes in this reference frame is also calibrated and known. BMD 2505 is proximated to the already implanted and malpositioned cup within the acetabulum, such as an attachment using an adaptor. The desired plane for impact ring 2510 is chosen and provided to navigation system 1715 and corresponds to the ultimate angle of abduction and anteversion that the surgeon desires for the implanted cup after the procedure. The following method for "dialing in" the desired plane is suggested. (Axes of BMD 2505 and impact ring 2510 are maintained in a neutral position (referred to herein as a double orthogonal position). For comfort of the surgeon, BMD 2505 is allowed to swivel within a specified cone (e.g., a thirty degree cone—other cone sizes are possible) while impact ring 2510 maintains the desired orientation as the angle between handle 2515 and impact ring 2510 changes to reflect the swiveling. BMD 2505 is swiveled around until the desired plane for impact ring 2510 in the reference frame of the operating room is established by navigation system 1715. This plane in the reference space is then registered by navigation system 1715, and will be set in the navigation system as the desired angle of abduction and anteversion for cup C. At that point the surgeon can move and swivel the gun in whatever position is comfortable for him/her during the procedure. BMD 2505 will then continuously make adjustments to maintain impact ring 2510 coplanar with the "desired plane". At this point no matter how the surgeon moves BMD 2505 in this 30 degree cone in space the mechanisms on BMD 2505 will make the automatic necessary adjustments to keep impact ring 2510 coplanar with the "desired plane" (e.g., 40 degrees abduction and 20 degrees anteversion). Once impact ring 2510 has been set to the desired plane, a tilt of handle 2515 by 5 degrees in one direction is countered by a corresponding five degree tilt of impact ring 2510 in an opposing direction to maintain impact ring 2510 at the desired plane.

The feedback loop system works in the following manner. Navigation system 1715 continuously and in real time measures the position and orientation of BMD 2505. Any positional change an axis of BMD 2505 (for example within this 30 degree cone) is measured by computer navigation system 1715 and relayed to microprocessor included with BMD 2505 as part of a stored program computing system implemented by BMD 2505 when using a control mechanism (e.g., servo motors coupled to impact ring 2510) to maintain impact ring 2510 in the desired plane using information from navigation system 1715. The microprocessor uses this information to compute an error between the "actual position" of BMD 2505 and the "desired position" of BMD 2505. The microprocessor converts this two dimensional special error into two one dimensional angular corrections and sends new commands to the control mechanism which will then make corrections to the position of impact ring 2510, moving it to the desired plane. The control mechanism, in addition, has an internal circuitry that is capable of maintaining a feedback loop mechanism, which functions to maintain the desired plane during swivels or other motions of BMD 2505 during operation. In this fashion, the BMD 2505 maintains impact ring 2510 position so that it is coplanar with the desired plane within the reference frame. BMD 2505 then strikes cup C with impact ring 2510 repeatedly until the mal-aligned cup is corrected to the desired position (i.e. 40 abduction and 20 anteversion in this example) at which point impact ring 2510 and the implanted cup become co-planer as illustrated in FIG. 24.

In other words, BMD 2505 functions as follows: BMD 2505 includes a microprocessor (circuit board) and one or more servos on board. These servos control the position of impact ring 2510 in the reference frame at all times. The BMD 2505 is attached to implanted cup C via an adaptor. BMD 2505 can swivel around a cone of 30 degrees while maintaining impact ring 2510 in the desired orientation as the servos compensate and adjust an orientation of impact ring 2510 to counter this swiveling motion. The surgeon moves BMD 2505 until the positioning is comfortable as the surgeon is going to use the device to impact the ring to re-orient cup C. BMD 2505 is moved around until the "desired plane" for the impact ring is found and registered in the reference frame (i.e. 40 abduction and 20 anteversion for this example) by navigation system 1715. The surgeon then moves BMD 2505 however desired and impact ring 2510 is automatically corrected to be the same as the "desired plane" at all times, regardless of how BMD 2505 is swiveled around. The surgeon then fires rapidly a repeating mechanical hammer that is coupled to impact ring 2510 rapidly causing the impact ring to hit on mal-aligned cup C until cup C and impact ring 2510 become coplanar, at which time the implanted cup's alignment has been corrected to the desired plane/alignment.

Some implementations with proper reconfiguring of current navigation systems will allow the desired plane (e.g., 40 degrees abduction and 20 degrees anteversion) to be calculated in the operating room reference frame space simply by knowing the plane of the acetabulum in the operating room space is (e.g., abduction 50 degrees, anteversion 10 degrees). Suggested methodology is through construction of a double orthogonal to the measured plane of the acetabulum in the operating room space. A change in the double orthogonal results in a change in the plane of the acetabulum. A positioning BMD could then know what this plane is without having its impact ring registered and calibrated by the navigation system.

Figure 26:
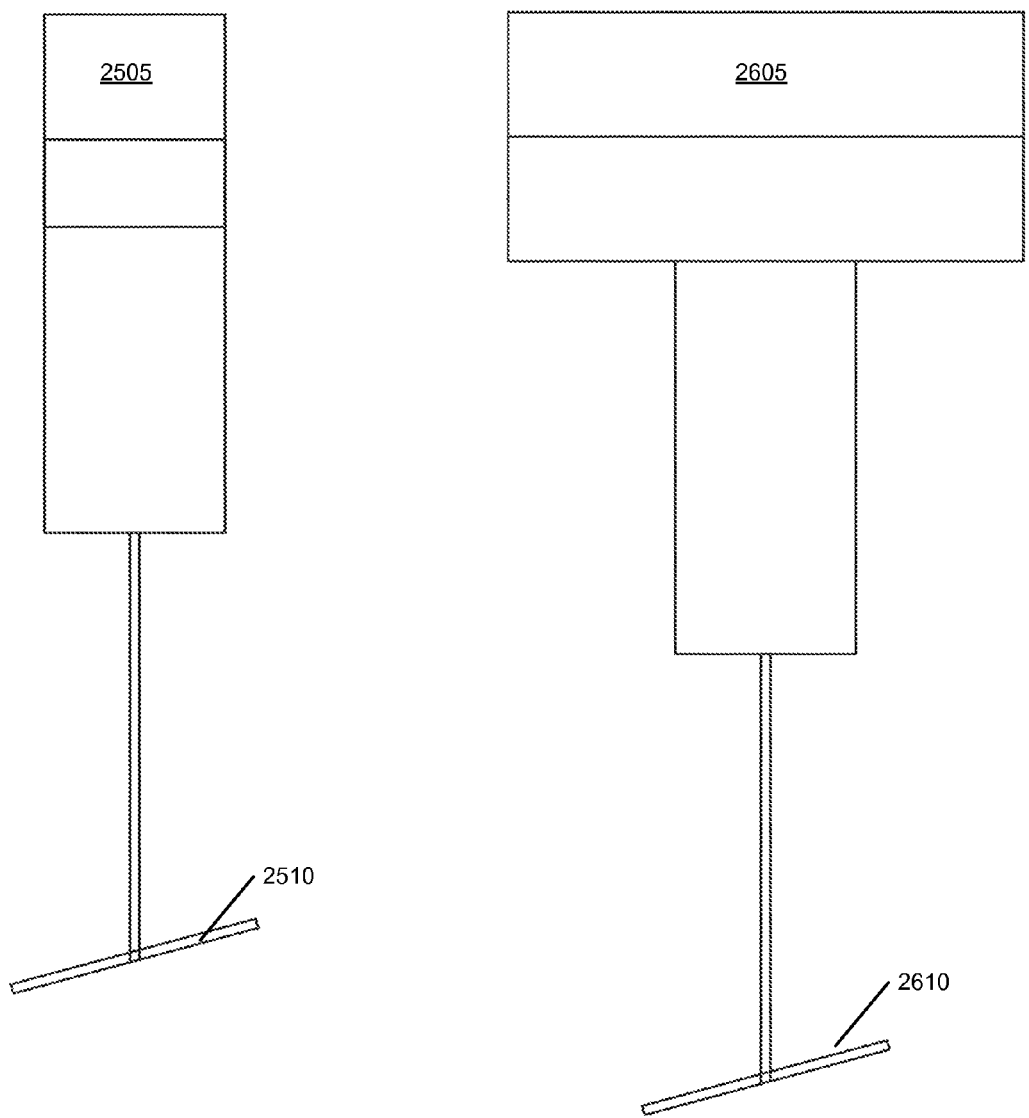
FIG. 26 illustrates an evolution of one version of a positioning system employing an impact ring, such as illustrated in FIG. 25, to another version of a positioning system employing an impact ring.

FIG. 26 illustrates an evolution of one version of a positioning BMD 2505 employing an impact ring 2510, such as illustrated in FIG. 25, to another version of a positioning BMD 2605 employing an impact ring 2610. During testing and evaluation of BMD 2505, it was discovered the impact ring positioning system (e.g., the servo motors) are required to have strength and stiffness as strikes of impact ring 2510 on the inserted cup are transferred to the servos. BMD 2605 includes a stiffer impact ring positioning system to allow the same real-time maintenance of the desired plane for impact ring 2610 while resisting problems associated with servo control. For example, worm gear or other microprocessor-controllable motor solution that provides a sufficient stiffness to allow portions of an impact ring to strike the mispositioned cup. The more misaligned an impact ring and cup are, the greater the angular differences are between the impact ring and the cup which can result in greater torsional/rotation response of the impact ring when striking the installed cup.

While BMD 2505 provided excellent information about the desired plane and was responsive to swiveling motion during use, it did not have the desired level of stiffness to hold the desired plane for the impact ring when striking the cup for repositioning. This is partially due to the observation that the impact ring does not provide a clean focus energy transfer mechanism due to the misalignment of the desired plane with the mispositioned cup and that the impact ring may be driven at the center while impacts are offset to an edge causing rotational stresses on the impact ring positioning system. While alternatives to the servos in BMD 2505, such as the direct current worm gear motor of BMD 2605 may improve stiffness, a drawback remains in the relatively inefficient energy transfer exists.

FIG. 27-FIG. 34 illustrate alternate embodiments for a positioning systems employing an impact ring model. FIG. 27-FIG. 28 illustrate a first alternate embodiment for a positioning system 2700; FIG. 27 illustrates a side view of the first alternate embodiment; and FIG. 28 illustrates a top view of the first alternate embodiment. Positioning system 2700 includes a positioning BMD 2705 having N number of actuators 2710 (N being an integer of 3 or more) are used to define a virtual impact ring using ends of the actuators (ends of three or more actuators define the desired plane). A prosthesis C is rotationally coupled to BMD 2705 using a pivot joint 2715. In this way, operation of a trigger 2720 causes all the actuators to strike prosthesis C concurrently at a peripheral edge. The actuators strike prosthesis C in the desired plane and more efficiently transfer repositioning energy to the edges of the cup. A computer navigation system is used to set the virtual impact ring.

FIG. 29-FIG. 30 illustrate a second alternate embodiment for a positioning system 2900; FIG. 29 illustrates a side view of the second alternate embodiment; and FIG. 30 illustrates a top view of the second alternate embodiment. Positioning system 2900 includes a positioning BMD 2905 having a single repositionable actuator 2910 used to define a virtual impact ring using an end of the actuator. A prosthesis C is rotationally coupled to BMD 2905 using a pivot joint 2915. In this way, operation of a trigger 2920 rotates actuator 2910 around a central support 2925 to locate actuator 2910 at the desired location around the periphery of cup C and then causes actuator 2910 to strike prosthesis C at a peripheral edge. Actuator 2910 strikes prosthesis C at the desired location to achieve the desired plane and more efficiently transfer repositioning energy to the edges of the cup. A computer navigation system is used to set the virtual impact ring. As actuator 2910 rotates about support 2925, a longitudinal extent of its end shortens or lengthens such that the end traces out a virtual impact ring having the desired plane over the course of an entire rotation about the support.

FIG. 31-FIG. 32 illustrate a third alternate embodiment for a positioning system 3100. FIG. 31 illustrates a side view of the third alternate embodiment; and FIG. 32 illustrates a top view of the third alternate embodiment. System 3100 includes a positioning BMD 3105 that conceptually combines BMD 1805 with BMD 2605. The actuators of BMD 1805 are very efficient in energy transfer (they transferred energy similar to mallet/tamp with minimal leakage). This was a desirable trait selected for this design. The impact ring of BMD 2605 was attractive in that the ideal position of the cup in the operating room reference frame space was always known and maintained by the positioning BMD.

With BMD 3105 the desired orientation information is now transferred back to the device itself. The position of a virtual impact ring is controlled by a special virtual impact ring controller having four (or more, for example 4-24) actuators 3110. The controlling unit that includes a microprocessor 3115, a motor driver 3120 with a rotatory encoder, a DC motor 3125, and worm gear 3130. This controlling unit would then maintain the position of virtual impact ring at all times in the operating room reference frame space. The virtual impact ring is defined by a plane created by the tips of the actuators (four in BMD 3105).

The tip of the four actuators are calibrated to allow the computer navigation system to know the position of the "virtual impact ring" in the operating room reference frame space. BMD 3105 is attached to an implanted cup C with an adaptor. The desired alignment is input by the surgeon into the computer navigation system. The computer navigation system provides information/commands to BMD 3105. The "controlling unit" of BMD 3105 maintains the position of the virtual impact ring in the operating room reference frame space, and then fires the four actuators 3110 in unison responsive to operation of a trigger 3135 hitting on a peripheral edge 3140 of the implanted cup C until the virtual impact ring (the tips of four actuators) and the implanted cup C are co-planer, achieving the desired correction.

Figure 33:
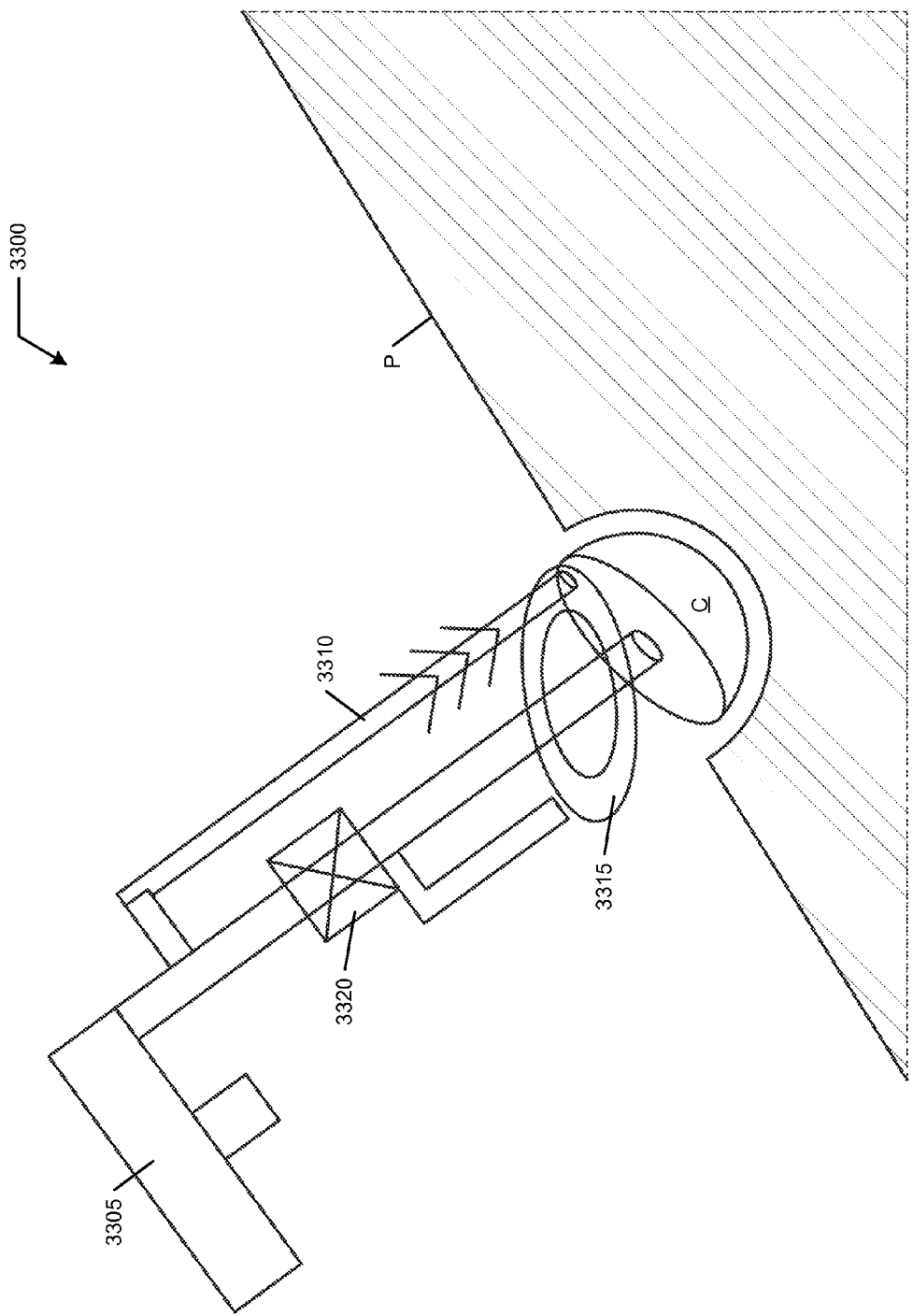

FIG. 33 illustrates a side view of a fourth alternate embodiment for a positioning system 3300 combining aspects of BMD 2505 and BMD 2905. System 3300 includes a positioning BMD 3305 that has a single repositionable actuator 3310 that strikes an mispositioned implanted cup C at a particular point on the edge to achieve a desired plane. The particular point is identified by an impact ring 3315 that is controlled by a servo 3320. In this case, servo 3320 is not part of the impacting construct as its function in this mode is to hold and define the desired plane. Impact ring 3315 is a slotted ring that serves to define the desired plane in the operating room frame of reference space. Single actuator 3310 rotates to the indicated position (which is the point of contact of the slotted ring with the implanted cup C) and impacts repeatedly on the edge of cup on this point until the slotted ring and the implanted cup C are co-planer. Servo 3320 and slotted impact ring 3315 provide the positional information on BMD 3305 and actuator 3310 provides focused high efficiency impacts on the edge of cup C to provide the desired change in cup alignment.

Figure 34:
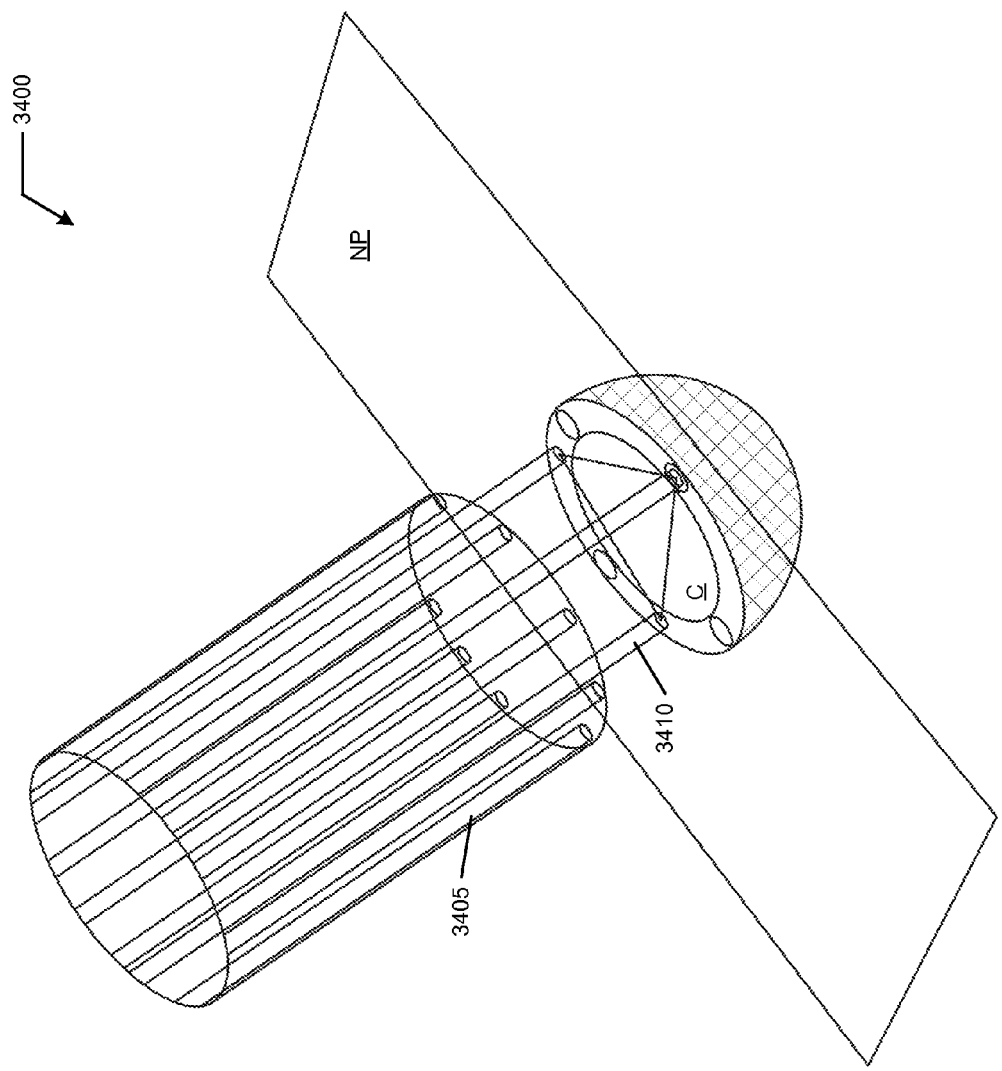

FIG. 34 illustrates a side view of a fifth alternate embodiment for a positioning system 3400 including a positioning BMD similar to BMD 1805 employing 12 actuators 3405 (with a 30 degree uniformly-spaced arcuate separation around a 360 cup periphery). The information for BMD 1805 was preferably encoded on the cup's edge using the computer navigation system. A potential drawback of BMD 1805 with some implementations was that there was not a mechanism to quickly measure a cup orientation after an impact and provide feedback to the computer navigation system. For some users, this measurement and feedback of information to the computer navigation system had to occur rapidly to allow the navigation system and the positioning BMD to perform multiple and rapid corrective hits on the cup through a feedback loop mechanism.

System 3400 reduces this problem by using three (or more) of the actuators as "plane calibrators" 3410. These actuators would serve both as impacting actuators and as plane calibrators. Much in the same way that the tips of the actuators in some embodiments were calibrated to define a 'virtual impact ring', the tips of these three special actuators 3410 are encoded and used to define a plane. So after each corrective hit is made by system 3400, the three actuators 3410 descend (slide down) and touch the edge of the cup at different locations (the position of which has just been adjusted). A new plane NP is defined. The position of this plane is conveyed back to the computer navigation system. The computer navigation system now calculates the difference between the new cup position and the desired cup position, (what has been dialed in by the surgeon). The computer then provides a new command based the new positional information it has just been given. A point on the cup is calculated to provide the desired change in alignment, the corresponding actuator 3405 fires to make another incremental change in the cup position. The position of the cup C is again measured by the sliding (plane calibrating) actuators 3410. The process is repeated until the desired alignment of the cup C is achieved (i.e., NP matches desired plane within the desired threshold). Ideally in the future the changes in the position of the cup can be measured with a light or laser system, obviating a need for the "sliding plane calibrating actuators" 3410. This change would allow more rapid measurement and acquisition of the cup's new position, relaying the information more rapidly to the navigation system. This allows system 3400 to make the necessary corrective hits very rapidly to obtain the desired cup alignment.

When tool such as the positioning BMD is developed, surgeons in general would be much more likely to adopt computer navigation for hip replacement surgery. In the US no more than 10% of surgeons use computer navigation systems for THR surgery. Improvements to this adoption is likely to occur for the following two reasons:

1. The surgeon is now assured that the extra time spent in the operating room will translate into a very meaningful difference: a perfect cup position. All surgeons will be happy to add an ½ hour to their operation for this simple goal.

2. Hip replacement surgery with navigation usually moves at a slower pace due to the fact that the surgeon continues to check the position of the instruments in relation to the pelvis. The surgeon will now be free to move more rapidly during the operation when it is known that at the end of the operation a reliable and effective tool is available to modify and correct the final position of the acetabular implant, in an automated and accurate fashion.

BMD allows all real time information technologies to utilize (a tool) to precisely and accurately implant the acetabular component (cup) within the pelvic acetabulum. BMD device coupled with use of navigation technology and fluoroscopy and (other novel measuring devices) is the only device that will allow surgeons from all walks of life, (low volume/high volume) to perform a perfect hip replacement with respect to acetabular component (cup) placement. With the use of BMD, surgeons can feel confident that they are doing a good job with acetabular component positioning, achieving the "perfect cup" every time. Hence the BMD concept eliminates the most common cause of complications in hip replacement surgery which has forever plagued the surgeon, the patients and the society in general.

It is known to use ultrasound devices in connection with some aspects of THR, primarily for implant removal (as some components may be installed using a cement that may be softened using ultrasound energy). There may be some suggestion that some ultrasonic devices that employ "ultrasound" energy could be used to insert a prosthesis for final fit, but it is in the context of a femoral component and it is believed that these devices are not presently actually used in the process). Some embodiments of BMD, in contrast, can simply be a vibratory device (non ultrasonic), most likely it will not be ultrasonic, and is more profound than simply an implantation device as it is most preferably a positioning device for the acetabular component in THR. Further, there is a discussion that ultrasound devices may be used to prepare bones for implanting a prosthesis. BMD does not address preparation of the bone as this is not a primary thrust of this aspect of the present invention. Some implementations of BMD may include a similar or related feature.

Some embodiments BMD include devices that concern themselves with proper installation and positioning of the prosthesis (e.g., an acetabular component) at the time of implanting of the prosthesis. Very specifically, it uses some form of vibratory energy coupled with a variety of "real time measurement systems" to POSITION the cup in a perfect alignment with minimal use of force. A prosthesis, such as for example, an acetabular cup, resists insertion. Once inserted, the cup resists changes to the inserted orientation. The BMDs of the present invention produce an insertion vibratory motion of a secured prosthesis that reduces the forces resisting insertion. In some implementations, the BMD may produce a positioning vibratory motion that reduces the forces resisting changes to the orientation. There are some implementations that produce both types of motion, either as a single vibratory profile or alternative profiles. In the present context for purposes of the present invention, the vibratory motion is characterized as "floating" the prosthesis as the prosthesis can become much simpler to insert and/or re-orient while the desired vibratory motion is available to the prosthesis. Some embodiments are described as producing vibrating prosthesis with a predetermined vibration pattern. In some implementations, the predetermined vibration pattern is predictable and largely completely defined in advance. In other implementations, the predetermined vibration pattern includes randomized vibratory motion in one or more motion freedoms of the available degrees of freedom (up to six degrees of freedom). That is, whichever translation or rotational freedom of motion is defined for the vibrating prosthesis, any of them may have an intentional randomness component, varying from large to small. In some cases the randomness component in any particular motion may be large and in some cases predominate the motion. In other cases the randomness component may be relatively small as to be barely detectable.

In the discussion herein, in addition to pure points defined for rotations of pure abduction, pure adduction, pure anteversion, and pure retroversion, in some implementations there are actuators that strike an inserted prosthesis at other locations intermediate a pair of pure points as described herein. These non-pure point strikes rotate the inserted prosthesis by a relative predetermined combination of abduction and retroversion (based on trigonometric contributions and degree of variation from the adjacent pure points). In this context, it is understood that the rotations may include negative values for abduction and/or anteversion, also referred to herein as adduction and retroversion, respectively. Also, for pure points, a quantity for one of the rotations is zero.

The system and methods above has been described in general terms as an aid to understanding details of preferred embodiments of the present invention. In the description herein, numerous specific details are provided, such as examples of components and/or methods, to provide a thorough understanding of embodiments of the present invention. Some features and benefits of the present invention are realized in such modes and are not required in every case. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

It will also be appreciated that one or more of the elements depicted in the drawings/figures can also be implemented in a more separated or integrated manner, or even removed or rendered as inoperable in certain cases, as is useful in accordance with a particular application.

Additionally, any signal arrows in the drawings/Figures should be considered only as exemplary, and not limiting, unless otherwise specifically noted. Combinations of components or steps will also be considered as being noted, where terminology is foreseen as rendering the ability to separate or combine is unclear.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letters Patent of the United States is:

1. An intraoperative system for positioning a mispositioned prosthetic cup inserted into a pelvic bone of a patient to within a first predetermined threshold of a desired orientation relative to a reference frame of the pelvic bone, the system using a position determining system establishing an intraoperative orientation of the mispositioned prosthetic cup, comprising: a positioning device including a set of actuators, said set of actuators having one or more actuators, said positioning device responsive to the intraoperative orientation to identify a group of actuators from said set of actuators, said group of actuators including at least one actuator configured to predictably re-orient the prosthetic cup within the pelvic bone responsive to a strike of the prosthetic cup by said group of actuators, said positioning device further including a selector activating said group of actuators and configured to initiate said strike at a location on the prosthetic cup predetermined to rotate the prosthetic cup within the reference frame by predefined relative rotation amounts of abduction and anteversion, wherein said set of actuators includes four actuators, wherein said location for a first actuator produces a pure abduction rotation of the prosthetic cup relative to the reference frame, wherein said location for a second actuator produces a pure adduction rotation of the prosthetic cup relative to the reference frame, wherein said location for a third actuator produces a pure anteversion rotation of the prosthetic cup relative to the reference frame, and wherein said location for a fourth actuator produces a pure retroversion rotation of the prosthetic cup relative to the reference frame.

2. The system of claim 1 wherein said set of actuators includes an additional eight actuators, wherein said locations for said additional eight actuators each produce a predetermined relative combination of abduction rotation and anteversion rotation, each said predetermined relative combination of abduction rotation and anteversion rotation for said additional eight actuators different from any other said predetermined relative combination of abduction rotation and anteversion rotation.

3. An intraoperative method for encoding a set of orthogonal pure points on a prosthetic cup inserted into a pelvic bone of a patient disposed on an operating table in an operating room, comprising:
  (a) establishing a frame of reference for the pelvic bone; and thereafter
  (b) mapping, using a robotic tool, the set of orthogonal pure points for the cup into said frame of reference, the set of orthogonal pure points including a first pure point for abduction, a second pure point for adduction, a third pure point for anteversion, and a fourth pure point for retroversion.

4. An automated intraoperative method for positioning a mispositioned prosthetic cup inserted into a pelvic bone of a patient to within a first predetermined threshold of a desired orientation relative to a reference frame of the pelvic bone, the system using a position determining system establishing an intraoperative orientation of the mispositioned prosthetic cup, comprising:
  (a) associating a positioning device to the prosthetic cup, said positioning device including a plurality of actuators uniformly distributed around a periphery of the prosthetic cup;
  (b) measuring intraoperatively a misposition of the prosthetic cup within the pelvic bone; and thereafter
  (c) actuating a set of one or more actuators of said plurality of actuators relative to a set of encoded pure points associated with the mispositioned prosthetic cup to rotate the mispositioned prosthetic cup in a correcting adjustment by a predetermined relative amount of abduction rotation and retroversion rotation, said correcting adjustment predictively reducing a magnitude of misposition of the prosthetic cup.

5. The method of claim 4 wherein said plurality of actuators includes four and wherein said actuators correspond to said set of encoded pure points.

6. The method of claim 4 wherein said plurality of actuators is greater than four and wherein four of said actuators correspond to said set of encoded pure points.

7. The method of claim 4 wherein said plurality of actuators includes three or more actuators and wherein one of said actuators corresponds to one pure point of said set of encoded pure points.

8. An orienting method for an inserted acetabular prosthesis that has been inserted into an installation site of a pelvis at an incorrect orientation relative to a desired orientation within a reference frame including the pelvis, the method comprising the steps of:
  a) encoding a set of pure points on a peripheral edge of the acetabular prosthesis relative to the reference frame, said set of pure points including a pure abduction point, a pure adduction point, a pure anteversion point, and a pure retroversion point;
  b) proximating a positioning device to the inserted acetabular prosthesis, said positioning device including an elongate column having an adapter configured to secure said positioning tool to a central rotation location of the inserted acetabular prosthesis producing a secured prosthesis while allowing relative rotation between said elongate column and said secured prosthesis, said positioning device including a set of actuators having at least one actuator coupled to said elongate column, spaced away from said peripheral edge, and configured to strike a location on said peripheral edge of said secured prosthesis;
  c) determining an orientation error between the incorrect orientation and the desired orientation relative to said set of pure points;
  d) determining an orientation adjustment location on said peripheral edge that decreases said orientation error when struck;
  e) positioning said at least one actuator relative to said orientation adjustment location; and
  f) operating said at least one actuator to perform a strike at said orientation adjustment location with said at least one actuator and decrease said orientation error responsive to said strike.

9. The orienting method of claim 8 wherein the reference frame comprises three orthogonal axes including an X axis, a Y axis, and a Z axis, wherein the reference frame includes a frontal plane constructed by said X axis and said Z axis, wherein the reference frame includes a transverse plane constructed by said X axis and said Y axis, wherein said orientation error includes a frontal plane error component and a transverse plane error component, wherein said frontal plane error component is decreased by striking a particular one frontal plane point selected from one of said pure abduction point or said pure adduction point; wherein said transverse plane error component is decreased by striking a particular one transverse plane point selected from one of said pure anteversion point or said pure retroversion point; and wherein said orientation adjustment location includes one of said particular one frontal plane point or said particular one transverse plane point.

10. The orienting method of claim 9 further comprising:
  g) positioning, after step f) said at least one actuator relative to a second orientation adjustment location including a different one of said particular one frontal plane point or said particular one transverse plane point; and
  f) operating said at least one actuator to perform a second strike at said second orientation adjustment location with said at least one actuator and decrease said orientation error responsive to said second strike.

11. The orienting method of claim 8 wherein said set of actuators provides four actuators evenly distributed around said elongate column.

12. The orienting method of claim 11 wherein the reference frame comprises three orthogonal axes including an X axis, a Y axis, and a Z axis, wherein the reference frame includes a frontal plane constructed by said X axis and said Z axis, wherein the reference frame includes a transverse plane constructed by said X axis and said Y axis, wherein said orientation error includes a frontal plane error component and a transverse plane error component, wherein said frontal plane error component is decreased by striking a particular one frontal plane point selected from one of said pure abduction point or said pure adduction point; wherein said transverse plane error component is decreased by striking a particular one transverse plane point selected from one of said pure anteversion point or said pure retroversion point; wherein said orientation adjustment location includes a combination of said particular one frontal plane point and said particular one transverse plane point; and wherein each said actuator corresponds to one pure point.

13. The orienting method of claim 12 wherein said positioning step e) positions one actuator at each said pure point and wherein said step f) includes operating said at least one actuator to perform said strike at said particular one frontal plane point and includes operating a different second actuator to perform a second strike at said particular one transverse plane point without repositioning said set of actuators.

14. The orienting method of claim 11 wherein said set of actuators provides one actuator associated with each said pure point.

15. The orienting method of claim 14 wherein said set of actuators further includes eight additional actuators evenly distributed around said elongate column.

16. The orienting method of claim 8 further comprising a computer navigation system configured to measure said orientation error and a post-strike error orientation after each said strike, further comprising:
  g) determining an intraprocedure orientation error between said post-strike error orientation and the desired orientation relative to said set of pure points;
  h) determining an intraprocedure orientation adjustment location on said peripheral edge that decreases said intraprocedure orientation error when struck;
  i) positioning said at least one actuator relative to said intraprocedure orientation adjustment location; and
  j) operating said at least one actuator to perform a subsequent strike at said intraprocedure orientation adjustment location with said at least one actuator and decrease said intraprocedure orientation error responsive to said subsequent strike; and
  k) repeating steps g)-j) until said post-strike error orientation is within a desired error.

17. A positioning tool for orienting an inserted acetabular prosthesis that has been inserted into an installation site of a pelvis at an incorrect orientation relative to a desired orientation within a reference frame including the pelvis, comprising:
  a handle including a trigger;
  an elongate column having a proximate end and a distal end opposite of said proximate end, said proximate end coupled to said handle, said elongate column defining a longitudinal axis extending from said proximal end to said distal end;
  a connector coupled to said distal end along said longitudinal axis, said connector defining a pivot point;
  an adapter rotationally coupled to said connector, said adapter configured for a rotation about said pivot point with at least two degrees of freedom for said rotation including a frontal rotation about a frontal plane passing through said pivot point and a transverse rotation about a transverse plane passing through said pivot point wherein said adapter includes an engagement system rigidly securing the acetabular prosthesis; and
  a set of actuators coupled to said elongate column, each said actuator of said set of actuators having an striker spaced away from said adapter and configured to couple a strike to a peripheral edge of the acetabular prosthesis when the acetabular prosthesis is rigidly secured to said adapter and said actuator is operated in response to activation of said trigger, the acetabular prosthesis rotating about said pivot point in response to said strike.

* * * * *